US008669357B2

(12) United States Patent
Carter et al.

(10) Patent No.: US 8,669,357 B2
(45) Date of Patent: *Mar. 11, 2014

(54) CELL SURFACE COATING WITH HYALURONIC ACID OLIGOMER DERIVATIVE

(75) Inventors: Nicola Lewell Carter, Auckland (NZ); Deborah Adella Blake, Auckland (NZ); Nicolai Bovin, Moscow (RU); Stephen Michael Henry, Auckland (NZ); Elena Yurievna Korchagina, Moscow (RU); Eleanor Christine Williams, Auckland (NZ); Alexander Tuzikov, Moscow (RU)

(73) Assignee: Kode Biotech Limited, Auckland (NZ)

( * ) Notice: Subject to any disclaimer, the term of this patent is extended or adjusted under 35 U.S.C. 154(b) by 0 days.

This patent is subject to a terminal disclaimer.

(21) Appl. No.: 13/459,365

(22) Filed: Apr. 30, 2012

(65) Prior Publication Data

US 2012/0277416 A1 Nov. 1, 2012

Related U.S. Application Data

(63) Continuation of application No. 11/992,408, filed as application No. PCT/NZ2006/000245 on Sep. 21, 2006, now Pat. No. 8,183,214.

(30) Foreign Application Priority Data

Sep. 21, 2005 (NZ) ........................................ 542568
Jul. 27, 2006 (NZ) ........................................ 548784

(51) Int. Cl.
*C08B 37/00* (2006.01)

(52) U.S. Cl.
USPC .......................................................... 536/53

(58) Field of Classification Search
None
See application file for complete search history.

(56) References Cited

U.S. PATENT DOCUMENTS

| | | | |
|---|---|---|---|
| 4,783,400 A | 11/1988 | Canova-Davis et al. | 435/7.9 |
| 5,064,817 A | 11/1991 | Yedgar et al. | |
| 5,942,246 A | 8/1999 | Mayhew et al. | 424/450 |

FOREIGN PATENT DOCUMENTS

| | | | |
|---|---|---|---|
| JP | 0930979 | | 2/1997 |
| WO | WO 0139815 | A2 | 6/2001 |
| WO | WO 01/51003 | A2 | 7/2001 |
| WO | WO 01/51003 | A3 | 7/2001 |
| WO | WO 02/22029 | A1 | 3/2002 |
| WO | WO 2006/050246 | A2 | 5/2006 |
| WO | WO 2006/050246 | A3 | 5/2006 |

OTHER PUBLICATIONS

Yerushalmi, et al; Archives of Biochemistry and Biophysics, vol. 349, No. 1, pp. 21-26, Jan. 1, 1998.
Gautam et al; Molecular Biotechnology, vol. 23, pp. 51-60 (2004).
Furnus; The Hyaluronic Acid Receptor (CD44) is Expressed in Bovine Oocytes and Early Stage Embryos; *Theriogenology*, vol. 60; pp. 1633-1644 (1980).
Ghosh, et al; Synthetic Glycolipids: Interaction with Galactose-binding Lectin and Hepatic Cells; *Archives of Biochemistry and Biophysics*; vol. 206, No. 2; pp. 445-457 (1981).
Eliaz, R.E., et al; "Liposome-encapsulated Doxorubicin Targeted to CD44: A Strategy to Kill CD44-overexpressing Tumor Cells[1]"; Cancer Research, vol. 61; pp. 2592-2601 (2001).
Oohira, A., et al; "Effects of Lipid-Derivatized Glycosaminoglycans (GAGs), a Novel Probe for Functional Analyses of GAGs, on Cell-to-Substratum Adhesion and Neurite Elongation in Primary Cultures of Fetal Rat Hippocampal Neurons[1]"; *Archives of Biochemistry and Biophysics*, vol. 378, No. 1; pp. 78-83 (2000).
Pacuszka, T., et al; "Neoglycolipid Analogues of Ganglioside $G_{M1}$ as Functional Receptors of Cholera Toxin"; *Biochemistry*, vol. 30, No. 10; pp. 2563-2570 (1991).
Peer, D., et al; "Loading Mitomycin C Inside Long Circulating Hyaluronan Targeted Nano-Liposomes Increases Its Antitumor Activity in Three Mice Tumor Models"; *Int. J. Cancer*; vol. 108; pp. 780-789 (2004).
Ruhela, D., et al; "Efficient Synthesis of an Aldehyde Functionalized Hyaluroic Acid and Its Application in the Preparation of Hyaluronan-Lipid Conjugates"; *Bioconjugate Chem.*, vol. 17; pp. 1360-1363 (2006).
Sugiura, N., et al; "Preparation of Lipid-derivatized Glycosaminoglycans to Probe a Regulatory Function of the Carbohydrate Moieties of Proteoglycans in Cell-Matrix Interaction"; *The Journal of Biological Chemistry*; vol. 268, No. 21; pp. 15779-15787 (1993).
Fenderson, et al; "Localization of Hyaluronan in Mouse Embryos During Implantation, Gastrulation and Organogenesis"; *Differentiation*, vol. 54; pp. 85-98 (1993).
Relucenti, et al; "Cumulus Oophorus Extracellular Matrix in the Human Oocyte: A role for Adhesive Proteins"; *International Journal of Anat. Embryol.*; vol. 110, No. 1, 2:219-214 (2005).
Simon, et al; "Hyaluronic Acid Can Successfully Replace Albumin as the Sole Macromolecule in a Human Embryo Transfer Medium"; *Fertility and Sterility*; vol. 79, No. 6; pp. 1434-1438 (2003).
Relucenti, M., et al; "Cumulus oophorus extracellular matrix in the human oocyte: a role for adhesive proteins"; *It. J. Anat. Embryol.*; vol. 110 (Supplemental), No. 2; pp. 219-224 (2005).
International Preliminary Report on Patentability, International Application No. PCT/NZ2006/000245; International Filing Date Sep. 21, 2006.
Fenderson, B., et al; "Localisation of hyaluronan in mouse embryos during implantation, gastrulation and organogenesis", *Differentiation*, vol. 54, pp. 85-98 (1993).
Simon, A; "Embryo transfer medium—hyaluronic acid in the place of albumin?"; *Fertility and sterility*, vol. 81, No. 4, pp. 1157-1158 (Apr. 2004).

*Primary Examiner* — Layla Bland
(74) *Attorney, Agent, or Firm* — Nixon & Vanderhye P.C.

(57) ABSTRACT

A method of localizing reproduction assisting hyaluronic acid to reproductive cell surfaces by covalently linking it to lipids is disclosed.

5 Claims, 11 Drawing Sheets

CELL SURFACE COATING WITH HYALURONIC ACID OLIGOMER DERIVATIVE

This application is a continuation of application Ser. No. 11/992,408 filed 3 Nov. 2008 now U.S. Pat. No. 8,183,214 which is a 371 of PCT/NZ2006/000245 filed 21 Sep. 2006, which claims priority to New Zealand Application Nos. 542568 filed 21 Sep. 2005 and 548784 filed 27 Jul. 2006, the entire contents of each of which are hereby incorporated by reference.

TECHNICAL FIELD

The invention relates to methods of localising carbohydrates to the surface of a cell or multi-cellular structure, and carbohydrate-lipid constructs for use in such methods.

In particular, the invention relates to carbohydrate-lipid constructs for localizing hyaluronic acid to the surface of a cell or multi-cellular structure and their use in methods of in vitro fertilisation and transplantation of embryos.

BACKGROUND ART

The development of cells and multi-cellular structures is influenced by the extracellular matrix (ECM). Hyaluronic acid (HA) is a major glycosaminoglycan component of the ECM.

HA is one of the most abundant glycosaminoglycans (GAGs) in the female reproductive tract (Lee and Ax (1984); Toole (1991)). Supplementation of both semi-defined and defined culture media with HA has been shown to improve the development of in vitro matured and fertilised bovine embryos to the blastocyst stage without affecting embryo quality and post-freeze survival.

The inclusion of HA in culture media has been proposed in order to increase the efficiency of in vitro blastocyst production from in vitro matured bovine oocytes (Furnus et al. (1998)). Indeed, in separate studies, the highest rates of implantation and foetal development after blastocyst transfer were observed when HA was the macromolecule in the culture media (Gardner et al. (1999)).

Several commercial embryo transfer media products supplemented with HA are available (EmbryoGlue® Vitrolife, UTM™ Medicult). Despite the availability of these products, the basis for the beneficial effects of HA on implantation and foetal development are not well understood.

HA may play a biophysical role mediating interactions between the embryo and the surface of the endometrium. Furnus et al., (1998) have suggested that HA might benefit embryo development per se, or regulate the action of factors synthesised by the embryo, acting in an autocrine manner.

Gardner et al. (1999) suggested that the highest cell numbers and hatching rates obtained in their study occurred when both serum albumin and HA were present in the same medium. It was proposed by these authors that embryo culture media should contain both serum albumin and HA, while transfer media need only contain HA.

It is an object of the invention to provide carbohydrate-lipid constructs for use in localising carbohydrate to the surface of embryos.

It is a further object of the invention to provide carbohydrate-lipid constructs for use in influencing the development of cells and multi-cellular structures.

It is a yet further object of the invention to provide a method for improving the likelihood of successful outcomes from assisted reproductive techniques.

These objects are to be read disjunctively with the object to at least provide the public with a useful choice.

DISCLOSURE OF INVENTION

In a first aspect the invention provides a method of localising hyaluronic acid to the surface of a cell or multicellular structure including the step of:

Contacting the cell or multicellular structure with a dispersion of a carbohydrate-lipid construct of the structure
F—$S_1$-$S_2$-L where:

F is an oligomer or polymer of hyaluronic acid consisting of β1-4 linked disaccharide units of glucuronic acid β1-3N-acetylglucosamine (GlcUAβ1-3GlcNAc);

$S_1$-$S_2$ is a spacer linking F to L; and

L is a lipid selected from the group consisting of diacyl- and dialkyl-glycerolipids, including glycerophospholipids.

Preferably F, $S_1$, $S_2$ and L are covalently linked.

Preferably F is 15-20 mer.

Preferably $S_1$-$S_2$ is selected to provide a water soluble construct that stably incorporates into a lipid bi-layer.

Preferably L is selected from the group consisting of: diacylglycerolipids, phosphatidate, phosphatidyl choline, phosphatidyl ethanolamine, phosphatidyl serine, phosphatidyl inositol, phosphatidyl glycerol, and diphosphatidyl glycerol derived from one or more of trans-3-hexadecenoic acid, cis-5-hexadecenoic acid, cis-7-hexadecenoic acid, cis-9-hexadecenoic acid, cis-6-octadecenoic acid, cis-9-octadecenoic acid, trans-9-octadecenoic acid, trans-11-octadecenoic acid, cis-11-octadecenoic acid, cis-11-eicosenoic acid or cis-13-docsenoic acid. More preferably the lipid is derived from one or more cis-desaturated fatty acids. Most preferably L is selected from the group consisting of: 1,2-O-dioleoyl-sn-glycero-3-phosphatidylethanolamine (DOPE), 1,2-O-distearyl-sn-glycero-3-phosphatidylethanolamine (DSPE) and rac-1,2-dioleoylglycerol (DOG).

In a first embodiment of the first aspect of the invention L is a glycerophospholipid and the carbohydrate-lipid construct includes the substructure:

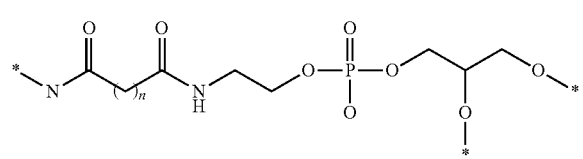

where n=3 to 5 and * is other than H. Preferably n is 3.

In a second embodiment of the first aspect of the invention L is a glycerolipid and the carbohydrate-lipid construct includes the substructure:

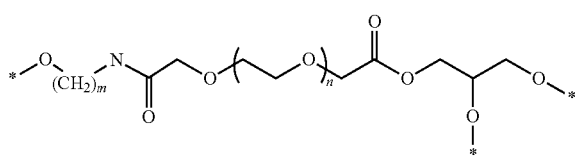

where * is other than H, m=3 to 5, and n=9 to 16. Preferably n is 10.

In the preferred third embodiment of the first aspect of the invention L is a glycerophospholipid and the carbohydrate-lipid construct includes the substructure:

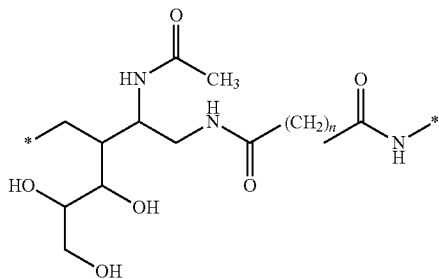

where n=3 to 5 and * is other than H. Preferably n is 3.

Preferably L is a glycerophospholipid.

Preferably F—$S_1$ is an oligomer or polymer of hyaluronic acid consisting of β1-4 linked disaccharide units of glucuronic acid β1-3N-acetylglucosamine (GlcUAβ1-3GlcNAc) linked to $S_2$ via a terminal glycamine residue (gar).

In a specific embodiment of the first aspect of the invention the carbohydrate-lipid construct has the structure:

L is a lipid selected from the group consisting of diacyl- and dialkyl-glycerolipids, including glycerophospholipids.

Preferably F, $S_1$, $S_2$ and L are covalently linked.

Preferably F is 15-20 mer.

Preferably $S_1$-$S_2$ is selected to provide a water soluble construct that stably incorporates into a lipid bi-layer.

Preferably L is selected from the group consisting of: diacylglycerolipids, phosphatidate, phosphatidyl choline, phosphatidyl ethanolamine, phosphatidyl serine, phosphatidyl inositol, phosphatidyl glycerol, and diphosphatidyl glycerol derived from one or more of trans-3-hexadecenoic acid, cis-5-hexadecenoic acid, cis-7-hexadecenoic acid, cis-9-hexadecenoic acid, cis-6-octadecenoic acid, cis-9-octadecenoic acid, trans-9-octadecenoic acid, trans-11-octadecenoic acid, cis-11-octadecenoic acid, cis-11-eicosenoic acid or cis-13-docsenoic acid. More preferably the lipid is derived from one or more cis-desaturated fatty acids. Most preferably L is selected from the group consisting of: 1,2-O-dioleoyl-sn-glycero-3-phosphatidylethanolamine (DOPE), 1,2-O-distearyl-sn-glycero-3-phosphatidylethanolamine (DSPE) and rac-1,2-dioleoylglycerol (DOG).

In a first embodiment of the second aspect of the invention L is a glycerophospholipid and the carbohydrate-lipid construct includes the substructure:

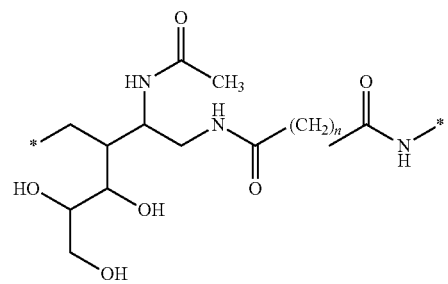

where n=3 to 5 and * is other than H. Preferably n is 3.

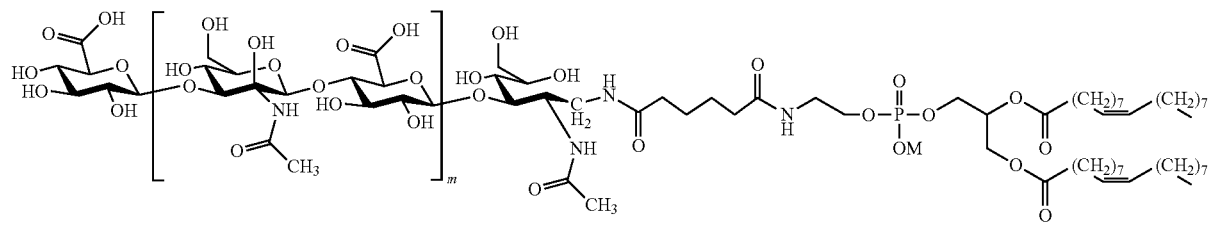

designated HA-gar-Ad-DOPE (IV).

M is typically H, but may be replaced by another monovalent cation such as $Na^+$, $K^+$ or $NH_4^+$.

In a second aspect the invention consists in a carbohydrate-lipid construct of the structure F—$S_1$-$S_2$-L where:

F is an oligomer or polymer of hyaluronic acid consisting of β1-4 linked disaccharide units of glucuronic acid β1-3N-acetylglucosamine (GlcUAβ1-3GlcNAc);

$S_1$-$S_2$ is a spacer linking F to L; and

Preferably L is a glycerophospholipid.

Preferably F—$S_1$ is an oligomer or polymer of hyaluronic acid consisting of β1-4 linked disaccharide units of glucuronic acid β1-3N-acetylglucosamine (GlcUAβ1-3GlcNAc) linked to $S_2$ via a terminal glycamine residue (gar).

In a specific embodiment of the second aspect of the invention the carbohydrate-lipid construct has the structure:

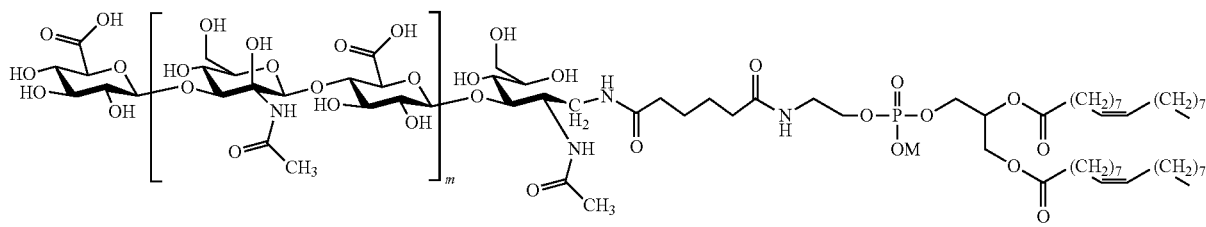

designated HA-gar-Ad-DOPE (IV)

M is typically H, but may be replaced by another monovalent cation such as $Na^+$, $K^+$ or $NH_4^+$.

In a third aspect the invention consists in a method of preparing a carbohydrate-lipid construct of the first embodiment of the second aspect of the invention of the structure F—$S_1$-$S_2$-L including the steps:
1. Reacting an activator ($A_1$) with a lipid (L) to provide an activated lipid ($A_1$-L);
2. Reductive amination of a carbohydrate (F) to provide (F—$S_1$); and
3. Condensing $A_1$-L with F—$S_1$ to provide the molecule;

F—$S_1$-$S_2$-L where:
$A_1$ is an activator selected from the group including: bis (N-hydronrsuccinimidyl), bis(4-nitrophenyl), bis(pentafluorophenyl), bis(pentachlorophenyl) esters of $C_5$-$C_7$ carbodioic acids;
L is a lipid selected from the group consisting of diacyl- and dialkyl-glycerolipids, including glycerophospholipids; and
F is a carbohydrate;

Preferably F is an oligomer or polymer of hyaluronic acid consisting of β1-4 linked disaccharide units of glucuronic acid β1-3N-acetylglucosamine (GlcUAβ1-3GlcNAc).

Preferably F is 15-20 mer.

Preferably $S_2$ is a $C_5$-$C_7$ aliphatic diacid. More preferably $S_2$ is a $C_5$-$C_7$ aliphatic diacid selected from the group consisting of: —CO(CH$_2$)$_3$CO—, —CO(CH$_2$)$_4$CO— (adipate), —CO(CH$_2$)$_5$CO— and —CO(CH$_2$)$_5$NHCO(CH$_2$)$_5$CO—.

Preferably L is selected from the group consisting of: diacylglycerolipids, phosphatidate, phosphatidyl choline, phosphatidyl ethanolamine, phosphatidyl serine, phosphatidyl inositol, phosphatidyl glycerol, and diphosphatidyl glycerol derived from one or more of trans-3-hexadecenoic acid, cis-5-hexadecenoic acid, cis-7-hexadecenoic acid, cis-9-hexadecenoic acid, cis-6-octadecenoic acid, cis-9-octadecenoic acid, trans-9-octadecenoic acid, trans-11-octadecenoic acid, cis-11-octadecenoic acid, cis-11-eicosenoic acid or cis-13-docsenoic acid. More preferably the lipid is derived from one or more cis-desaturated fatty acids. Most preferably L is selected from the group consisting of: 1,2-O-dioleoyl-sn-glycero-3-phosphatidylethanolamine (DOPE), 1,2-O-distearyl-sn-glycero-3-phosphatidylethanolamine (DSPE) and rac-1,2-dioleoylglycerol (DOG).

In a preferred embodiment L is a glycerolipid and the carbohydrate-lipid construct includes the substructure:

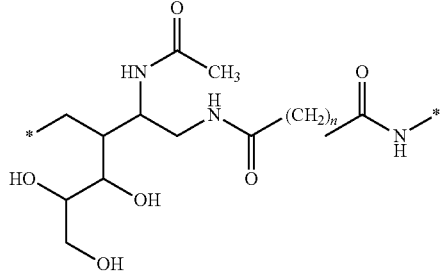

where n=3 to 5 and * is other than H. Preferably n is 3.

Preferably L is a glycerophospholipid.

In a specific embodiment the carbohydrate-lipid construct has the structure:

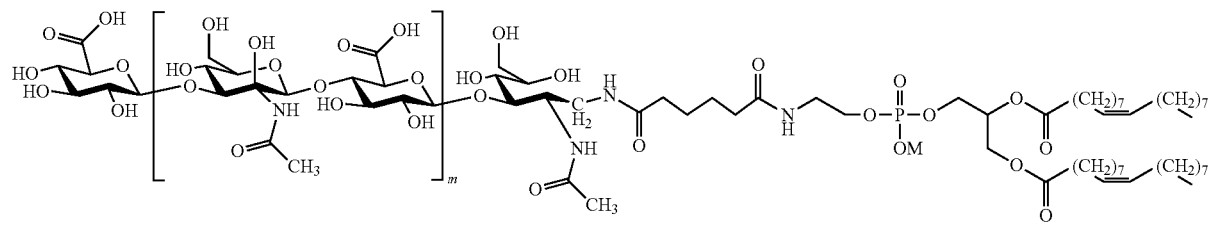

designated HA-gar-Ad-DOPE (IV).

M is typically H, but may be replaced by another monovalent cation such as $Na^+$, $K^+$ or $NH_4^+$.

In a fourth aspect the invention consists in a carbohydrate-lipid construct prepared by a method according to the third aspect of the invention.

In a fifth aspect the invention broadly consists in a method of assisted reproduction including the step of:
contacting an embryo with a carbohydrate-lipid construct of the second aspect or fourth aspect of the invention.

In a sixth aspect the invention broadly consists in a method of in vitro maturation of an embryo including the step of:
contacting the embryo with a carbohydrate-lipid construct of the second aspect or fourth aspect of the invention.

In a seventh aspect the invention broadly consists in a method of transferring an embryo to the endometrium with an improved likelihood of a successful outcome, including the step of:

contacting the embryo with a carbohydrate-lipid construct of the second aspect or fourth aspect of the invention.

In a eighth aspect the invention consists in medium including a dispersion of carbohydrate-lipid construct according to the second aspect or fourth aspect of the invention.

Preferably the medium is an ART or IVM medium.

In an ninth aspect the invention consists in a medicinal formulation including a carbohydrate-lipid construct according to the second aspect or fourth aspect of the invention.

Preferably the formulation is in a form suitable for inhalation. More preferably the formulation is in the form of an aerosol suitable for inhalation.

In the context of this description the following terms and phrases have the meanings provided:

"ART" means assisted reproductive techniques including, but not limited to, IVF and IVM methods.

"HA" denotes an oligomer or polymer of HA consisting of β1-4 linked disaccharide units of glucuronic acid β1-3N-acetylglucosamine (GlcUAβ1-3GlcNAc).

"Dispersion" means in reference to a carbohydrate-lipid construct an homogenous suspension or solution of the construct with or without the inclusion of dispersants or detergents.

"IVF" means the methods through which male and female gametes are brought into contact outside the body in order to accomplish fertilization.

"IVM" means the methods of in vitro maturation of embryos.

"Improved likelihood of a successful outcome" means, in relation to transferring an embryo to the endometrium, an increased likelihood of the transplanted embryo implanting and developing to provide a live birth.

"Stably incorporates" means that the carbohydrate-lipid construct incorporates into the lipid bi-layer or membrane for a time sufficient to effect a change in a biological activity of the transformed cell or multi-cellular structure.

"Water soluble" means a stable, single phase system (including a "dispersion" as defined above) is formed when the carbohydrate-lipid construct is contacted with water or saline (such as PBS) in the absence of organic solvents or detergents.

Exemplary embodiments of the invention will now be described in detail with reference to the Figures of the accompanying drawings pages.

DETAILED DESCRIPTION

Figure 1:
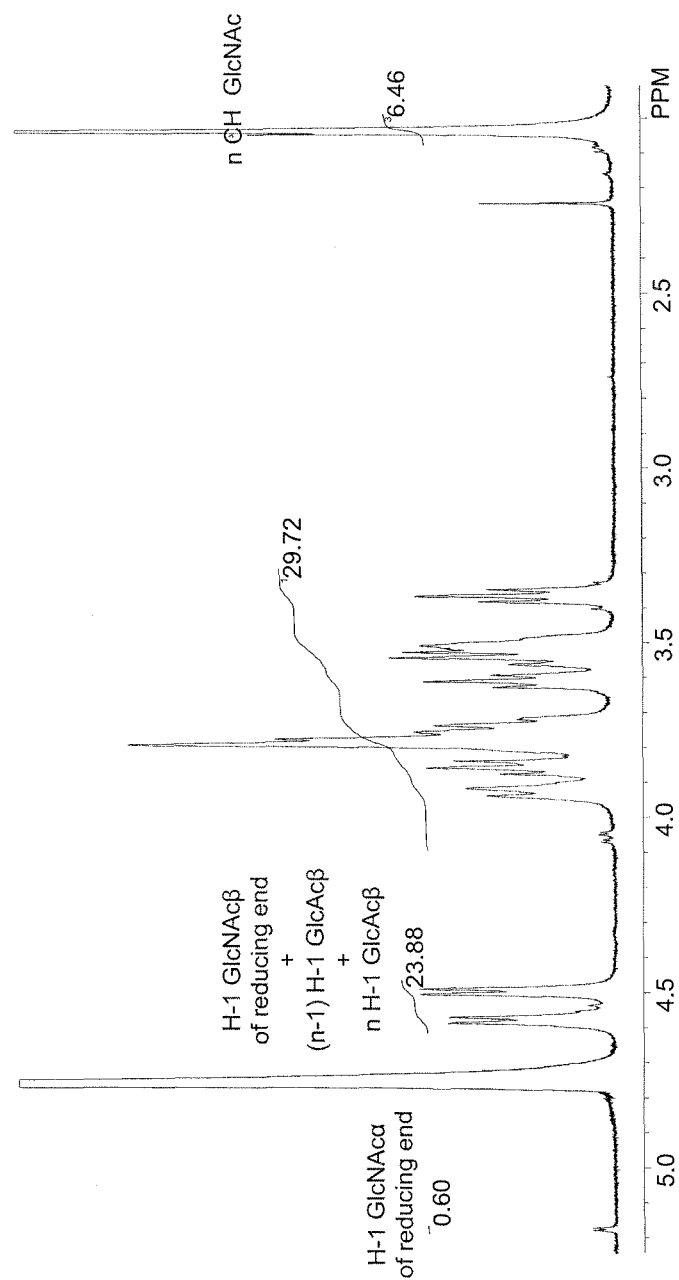
FIG. 1—$^1$H NMR spectrum of HA$_{10-14\ mer}$ (D$_2$O, 303K, δ ppm) (I).

Hyaluronic acid (HA) is a linear polymer, composed of repeating disaccharides of glucuronic acid (GlcUA) and N-acetyl-D-glucosamine (GlcNAc). The polymer can reach a molecular mass of several million Daltons and is a ubiquitous component of extracellular matrices, where it is often associated with HA binding proteoglycans and HA binding proteins.

CD44 is a broadly distributed cell surface protein thought to mediate cell attachment to extracellular matrix components or specific cell surface ligands. CD44 is the principal cell surface receptor for HA.

The binding of HA at the cell surface is a complex interplay of multivalent binding events affected by the size of the multivalent HA ligand. The minimum receptor binding site is a hexasaccharide composed of three repeats of β1-4 linked disaccharide units of glucuronic acid β1-3N-acetylglucosamine (GlcUAβ1-3GlcNAc).

The overall size of the HA polymer influences binding. Longer HA polymers result in more receptor-ligand interactions, thus reducing the probability of dissociation. Monovalent binding between HA and CD44 is thought to be optimised for a decasaccharide, although significant binding occurs with the hexasaccharide. An increase in binding avidity for HA consisting of between 20 and 24 saccharides indicates the point at which divalent binding to CD44 occurs.

HA oligomers and polymers of different sizes are known to elicit different biological activities. The selection of oligomers or polymers of different sizes to elicit different biological responses is contemplated by the inventors.

Methods for obtaining HA oligosaccharides of uniform size have been described (Tawada et al. (2002)). Oligosaccharides are prepared by the digestion of HA polymer with testicular hyaluronidase enzyme that hydrolyses the β1-4 glycosidic bond.

The inventors propose that by localising HA to the surface of a cell or multi-cellular structure different biological activities may be elicited. Where the multi-cellular structure is an embryo improvements may be achieved in one or more of:

the growth characteristics of the embryo;
the storage characteristics of the embryo;
the survival of the embryo; and/or
the likelihood of implantation of the embryo following transfer to the uterus.

In respect of this latter improvement oligosaccharides of HA of sufficient length to enable associative interaction with CD44 expressed on the surface of endometrial cells of the recipient host is desired. Indeed, longer oligosaccharides are likely to favour stronger association with these endometrium expressed receptors.

Acknowledging the observations of other investigators the inventors do not discount the possibility of oligosaccharides of HA localised to the surface of the embryo providing improvements in other areas, such as embryo growth characteristics. Indeed, the method of the invention may promote internalisation of surface localised HA, with consequential effects on intracellular signalling and embryo development.

The carbohydrate-lipid constructs may have other medicinal applications where localization of carbohydrate to the surface of a cell or multi-cellular structure is advantageous.

For example, the carbohydrate-lipid construct designated HA-gar-Ad-DOPE (IV) is particularly suited for use in the manufacture of medicinal formulations. The construct is soluble in aqueous media, but readily and stably incorporates into the membranes of cells (e.g. red blood cells) and multi-cellular structures (e.g. embryos).

A proven method of preparing the carbohydrate-lipid construct designated HA-gar-Ad-DOPE (IV) is provided in Scheme I. Difficulties have been shown to arise in the preparation of carbohydrate-lipid constructs comprising HA by other methods as discussed below. However, the inventors contemplate the feasibility of preparing a range of carbohydrate-lipid constructs comprising HA with similar favourable properties.

These carbohydrate-lipid constructs are distinguished from those prepared by the methods described in the specifications accompanying international application no. PCT/NZ02/00214 (WO 03/034074) and PCT/NZ03/00059 (WO 03/087346).

The methods of localising a carbohydrate to the surface of the cell or multi-cellular structure described in these specifications require the use of an endogenously prepared (biosynthesised) glycolipid or the use of a biotinylated lipid that is first incorporated into the lipid bi-layer.

The synthetic carbohydrate-lipid constructs of the present invention are exogenously prepared and do not comprise biotin-avidin bridges as a spacer ($S_1$-$S_2$) linking the carbohydrate (F) to the lipid (L). F, $S_1$, $S_2$ and L of the carbohydrate-lipid constructs are covalently linked and can be used in a one step method of localising the carbohydrate to the surface of the cell or multi-cellular structure.

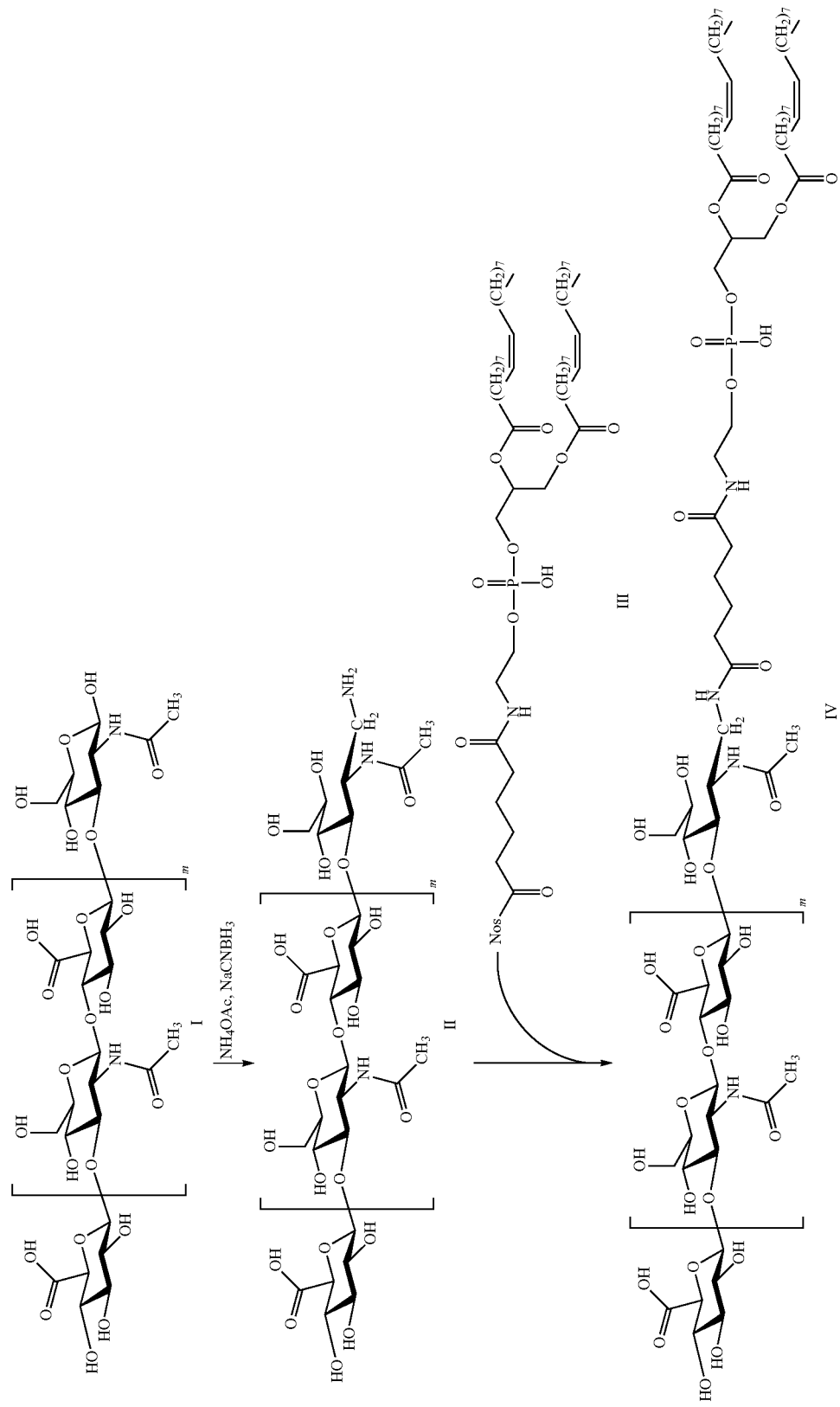

BEST MODE FOR CARRYING OUT THE INVENTION

Preparation of Carbohydrate-Lipid Constructs

Materials and Methods

Methanol, i-PrOh, $CH_2Cl_2$, diethyl ether, hexane and $NH_4OAc$ were from Chimed (Russia). Acetonitrile was from Cryochrom (Russia). Silica gel 60 RP-18 (40-63 μm) and $NaCNBH_3$ were from Merck (Germany). Sephadex G-10 and Sephadex LH-20 were from Amersham Biosciences AB (Sweden).

Thin-layer chromatography was performed on silica gel 60 F254 plates (Merck). Compounds were detected by staining with 8% phosphoric acid in water followed by heating at over 200° C., or ninhydrine as indicated.

For activated lipids $^1$H NMR spectra were acquired on a Bruker DRX-500 spectrometer. Chemical shifts are given in ppm (δ) relative to $CD_3OD$.

For HA-lipid constructs $^1$H NMR spectra were acquired at 30° C. on a Bruker WM 500 MHz instrument using the signal of the solvent's residual protons as reference (for $[D_2]H_2O$-4.750 ppm).

Activated lipids were prepared as either the adipate derivative of glycerophospholipids (Method 1) or the [p-notrophenoxycarbonylmethylene (polyoxyethylene)]-oxyacetyl derivative of diacyl glycerolipids (Method 2).

Preparation of Activated Lipids

Method 1 (Preparation of adipate derivative of 1,2-O-distereoyl-sn-glycero-3-phosphatidylethanolamine (DSPE) and 1,2-O-dioleoyl-sn-glycero-3-phosphatidylethanolamine (DOPE))

To a solution of bis(N-hydroxysuccinimidyl) adipate (A) (70 mg, 205 μmol) in dry N,N-dimethylformamide (1.5 ml) were added DOPE or DSPE (L) (40 μmol) in chloroform (1.5 ml) followed by triethylamine (7 μl). The mixture was kept for 2 h at room temperature, then neutralized with acetic acid and partially concentrated in vacuo.

Column chromatography (Sephadex LH-20, 1:1 chloroform-methanol, 0.2% acetic acid) of the residue yielded the activated lipid (A-L) (37 mg, 95%) as a colorless syrup; TLC (chloroform-methanol-water, 6:3:0.5): $R_f$=0.5 (DOPE-A; III), $R_f$=0.55 (DSPE-A).

$^1$H NMR ($CDCl_3/CD_3OD$, 2:1), δ:

DSPE-A—5.39 (m, 1H, —$OCH_2$—CHO—$CH_2O$—), 4.53 (dd, 1H, J=3.42, J=11.98, —CCOOHCH—CHO—$CH_2O$—), 4.33 (dd, 1H, J=6.87, J=11.98, —CCOOHCH—CHO—$CH_2O$—), 4.23 (m, 2H, PO—$CH_2$—$CH_2$—$NH_2$), 4.15 (m, 2H, —$CH_2$—OP), 3.61 (m, 2H, PO—$CH_2$—$CH_2$—$NH_2$), 3.00 (s, 4H, ONSuc), 2.81 (m, 2H, —$CH_2$—CO (Ad), 2.48 (m, 4H, 2×(—$CH_2$—CO), 2.42 (m, 2H, —$CH_2$—CO (Ad), 1.93 (m, 4H, $COCH_2CH_2CH_2CH_2CO$), 1.78 (m, 4H, 2×($COCH_2CH_2$—), 1.43, 1.47 (2 bs, 40H, 20$CH_2$), 1.04 (m, 6H, 2$CH_3$).

DOPE-A (III)—5.5 (m, 4H, 2×(—CH═CH—), 5.39 (m, 1H, —$OCH_2$—CHO—$CH_2O$—), 4.58 (dd, 1H, J=3.67, J=11.98, —CCOOHCH—CHO—CH2O—), 4.34 (dd, 1H, J=6.61, J=11.98, —CCOOHCH—CHO—$CH_2O$—), 4.26 (m, 2H, PO—$CH_2$—$CH_2$—$NH_2$), 4.18 (m, 2H, —$CH_2$—OP), 3.62 (m, 2H, PO—$CH_2$—$CH_2$—$NH_2$), 3.00 (s, 4H, ONSuc), 2.8 (m, 2H, —$CH_2$—CO (Ad), 2.50 (m, 4H, 2×(—$CH_2$—CO), 2.42 (m, 2H, —$CH_2$—CO (Ad), 2.17 (m, 8H, 2×(—$CH_2$—CH═CH—$CH_2$—), 1.93 (m, 4H, $COCH_2CH_2CH_2CH_2CO$), 1.78 (m, 4H, 2×($COCH_2CH_2$—), 1.43, 1.47 (2 bs, 40H, 20$CH_2$), 1.04 (m, 6H, 2$CH_3$).

Method 2 (Preparation of rac-1,2-Dioleoyl-3-[p-nitrophenoxycarbonylmethylene(polyoxyethylene)]-oxyacetylglycerol)

Biscarboxymethyl ether of polyethylene glycol (polymerization degree of 9-16) is dried by co-evaporation with benzene and subsequent stored under vacuum. Thionyl chloride (0.86 ml, 12 mmol) is added dropwise to a stirred mixture of diacid (0.6 g, ~1 mmol) and heated $Na_2CO_2$ (0.42 g, 4 mmol).

The reaction mixture is stirred at room temperature until gas evolution ceased (~4 h), evaporated, and twice resuspended in ethyl ether and evaporated for the removal of residual thionyl chloride. The residue is resuspended in ethyl ether and filtered through Kieselgur.

The upper phase of the filtrate with separated phases is evaporated. The residue is dissolved in dry dioxane, evaporated, and dried in a vacuum over NaOH to give diacid dichloride of carboxymethyl [poly(oxyethylene)]oxyacetic acid (D).

A solution of rac-1,2-dioleoylglycerol (DOG; L) (90 mg, 0.14 mmol) and triethylamine (0.1 ml, 0.72 mmol) in dry chloroform (3 ml) is added with stirring to diacid dichloride (D) (0.59 g, ~0.89 mmol). The reaction is carried out with stirring at room temperature for 24-36 h (TLC monitoring in systems B and C) with an occasional addition of triethylamine (10 μl portions, 0.2 ml in total).

The reaction mixture is diluted with chloroform (~10 ml) and washed with 0.1N HCl (10 ml) (phases separated by centrifugation). The aqueous phase is twice extracted with chloroform. The combined organic extracts are washed with water and evaporated. The residue is dried by co-evaporation with benzene and applied onto a gel filtration column (1×100 cm) equilibrated with solvent system A to give a mixture of mono- and di-acylation products.

The mixture is separated by chromatography on a silica gel column in a gradient of 10:1 methanol-acetic acid solution in chloroform (from 2 to 10%) to give (D-L) as a colorless oil; Rf~0.6 (B, elongated spot); MS, m/z: 1149.9 m/z: 1149.9 $[M+H_2O-1]^+$ (36), 1194.1 $[M+H_2O-1]^+$ (69), 1238.1 $[M+H_2O-1]^+$+(100), 1282.0 $[M+H_2O-1]^+$ (92), 1326.0 $[M+H_2O-1]^+$ (85), 1370.3 $[M+H_2O-1]^+$ (75), 1414.2 $[M+H_2O-1]^+$ (60), and 1458.1 $[M+H_2O-1]^+$ (42); $^1$H NMR ($CD_3OD$): 1.09 (6H, t, $CH_3$), 1.50 (40H, m $CH_2$), 1.80 (4H, br. quintet, $CH_2CH_2COO$), 2.23 (8H m, $CH_2CH$═CH), 2.52 (4H, t, $CH_2COO$), 3.83 (52H m, $OCH_2CH_2O$), 4.31 (2H, s, $OCH_2COO$-diglyceride), 4.38 (2H, s, $OCH_2COOH$), 4.48 and 4.59 (4H, a set of multiplets, C1' and C3'), 5.48 (1H, m, C2'), 5.54 (4H, m, CH═CH).

A solution of p-nitrophenyl trifluoroacetate (52 mg, 0.22 mmol) in dry pyridine (0.2 ml) is added to acid (D-L) (85 mg, ~0.07 mmol) and stirred at room temperature for 7 h. The reaction mixture is separated on a Sephadex LH-20 column (0.8×50 cm) equilibrated with solvent system A supplemented with 1% $CH_2COOH$ to yield ($A_2$-D-L) as a light yellow chromatographically homogeneous oil; Rf 0.75 (D; a, b, c).

$^1$H NMR:

DOG-D-$A_2$—0.88 (6H, t, $CH_3$), 1.29 (40H, m, $CH_2$), 1.61 (4H, m, $CH_2CH_2COO$), 2.01 (8H, m, $CH_2CH$═CH), 2.31 (4H, t, $CH_2COO$), 3.65 (52H, m, $OCH_2CH_2O$), 4.16 (2H, s, $OCH_2COO$-diglyceride), 4.17 (2H, s, t $OCH_2COONp$), 4.22, 4.29, and 4.38 (4H, a set of dd, C1' and C3'), 5.27 (1H, br.

quintet, C2'), 5.35 (4H, m, CH═CH), 7.34 (2H, d, J2'3'=J5'6'=9.15, H2', H6'), 8.29 (2H, d, J3'2'=J5'6'=9.15, H3', H5')

The activated lipids prepared by Method 1 or Method 2 may be condensed with the primary amine of a carbohydrate derivative to provide a carbohydrate-lipid construct.

Condensing Activated Lipid with Aminopropyl-HA

Condensing activated lipid with the aminopropyl derivative of hyaluronic acid according to either of the following prophetic methods was found to provide low to no yield of carbohydrate-lipid construct.

Method 3

To a solution of activated DOPE ($A_1$-L) (33 μmol) in N,N-dimethylformamide (1 ml) 30 μmol of 3-aminopropyl glycoside of HA and 5 μl of triethylamine is added. The mixture is stirred for 2 h at room temperature. Column chromatography (Sephadex LH-20 in 1:1 chloroform-methanol is followed by silica gel in ethyl acetate-isopropanol-water, 4:3:1 (v/v/v).

Method 4

To a solution of the ester ($A_2$-D-L) (~6.25 μmol) in dry DMSO (0.2 ml) and TEA (3 μl, 20 μmol) is added to 3-aminopropyl glycoside of HA (6.48 μmol). The reaction mixture is stirred at room temperature for 24 h, mixed with a drop of water, and separated on a gel filtration column (0.6×35 cm) equilibrated with solvent system A.

The failure of these methods of preparation was attributed to the instability of the 3-aminopropyl glycoside of HA in solution. An alternative method of preparing a primary amine of the carbohydrate hyaluronic acid was therefore developed (Scheme I).

The reductive amination of HA provided a carbohydrate with a terminal glycamine residue (gar) that could then be condensed with an activated lipid such as rac-1,2-dioleoyl-3-[p-nitrophenoxycarbonylmethylene(polyoxyethylene)]-oxyacetylglycerol (DOG) to provide a range of carbohydrate-lipid constructs.

In the following exemplary method HA is condensed with the N-oxysuccinimide ester DOPE-Ad-Nos via a terminal glycamine residue (gar).

Preparation of HA-Glycamine (II)

HA ($HA_{15-20\ mer}$) (I) (36 mg) was dissolved in 5M $NH_4OAc$ (3.6 mL). The solution was kept for 21 h at 40° C. After addition of aqueous 2M $NaCNBH_3$ in five sequential portions (40 μL of 2M $NaCNBH_3$—for 3 h; 80 μL—18 h; 160 μL—8 h; 160 μL—21 h; 160 μL—21 h) the mixture was kept at 40° C.

Desalting of the reaction mixture by gel-permeation chromatography on a Sephadex G-10 column (1.8×40 cm, eluent—aqueous 0.1M Py.AcOH) and freeze-drying gave 32.8 mg of HA-glycamine (II) in admixture with I.

TLC (eluent i-PrOH/MeOH/MeCN/water 4:3:6:4): HA-glycamine (II) (ninhydrine-positive) $R_f$=0.2; HA oligomer (I) $R_f$=0.31.

Preparation of HA-gar-Ad-DOPE (IV)

HA-glycamine (II) (32.8 mg) was dissolved in the mixture of i-PrOH (1.5 mL) and water (0.75 mL). To the rapidly stirred solution of II a solution of N-oxysuccinimide ester DOPE-Ad-Nos (III) (34 mg, 35 μM) in $CH_2Cl_2$ (0.2 mL) was added followed by aqueous 1M $Na_2CO_3$ in two portions (85 and 45 μl) with 45 min interval. The mixture was stirred for 45 min and then acidified with AcOH (30 μL).

Gel-permeation chromatography of the reaction mixture on Sephadex LH-20 column (1.8×35 cm, eluent—MeCN/water 2:1, 0.03M Py.AcOH) gave 42.5 mg of HA-gar-Ad-DOPE (IV) in admixture with I.

Separation of HA Oligomer (I) and HA-gar-Ad-DOPE (IV)

A solution of the crude product in water was slowly put on a C18 reverse phase column (1.2×7 cm, water). Elution with water and water/MeOH 10:1 provided I (12.3 mg). Elution with water/MeOH 1:3 and then with water/MeOH/CHCl3 5:15:1 gave IV.

This fraction was evaporated and the residue (thin film on the flask walls) was extracted with hexane (2×2 mL) and ether (2×2 mL) then dissolved in water (1.5 mL) and freeze-dried.

Yield of IV was 20.6 mg (~50%).

TLC: $R_f$=0.33, eluent i-PrOH/MeOH/MeCN/water 4:3:6:4.

$^1$H NMR of IV, Na-salt (500 MHz, $D_2O$, 2 mM $NaHCO_2$, 30° C.): δ=5.473 (m, 2 —CH═CH— of DOPE), 5.328 (m, $OCH_2CHCH_2O$ of DOPE), 4.574 and 4.473 (m, HA: H–1 of GlcNAc, H–1 of GlcA; CO—$OCHCHCH_2$ of DOPE), 4.246 (dd, J=12.3 Hz, J=6.8 Hz, CO—$OCHCHCH_2$ of DOPE), 4.027 (t, J=5.7 Hz, $POCH_2CH_2N$ of DOPE), 3.95-3.34 (HA: H–2÷H–6 of GlcNAc, H–2÷H–5 of GlcA; $POCH_2CHCH_2$ of DOPE), 2.413 (m, 2 $CH_2COO$ of DOPE), 2.302 (m, 2 $CH_2CON$), 2.049 (m, 2 $CH_2CH═CHCH_2$ of DOPE), 2.039 (m, $NCOCH_2$ of GlcNAc), 1.630 (m, 2 $CH_2CH_2CON$ and 2 $CH_2CH_2COO$ of DOPE), 1.306 (m, —$CH_2$— of DOPE), 0.892 (~t, 2 $CH_2$ of DOPE) ppm.

Approximation of Size of HA Oligomer Used in the Synthesis of HA-gar-Ad-DOPE (IV)

The average "n" value of the HA oligomer of the HA-gar-Ad-DOPE construct (IV) was considered to be the same as that of starting HA oligomer (I).

For an $HA_{n1-n2\ mer}$ the average "n" value may be estimated by $^1$H-NMR. Assuming the GlcNAc reducing end ratio α/β to be 60/40 (the normal ratio for free GlcNAc) the average "n" value for $HA_{10-14\ mer}$ was calculated as ~12.2 (FIG. 1). For $HA_{15-20\ mer}$ (I) this approach provided an average "n" value of ~13.

Insertion of Ha-Gar-Ad-Dope (Iv) into Red Blood Cell Membranes.

Packed Group O cells were washed three times with PBS by adding 7× the amount of PBS to RBC in a test tube. A Pasteur pipette washed used to gently mix the contents of the test tube. The test tube was centrifuged for 1 minute on at low speed in order to get the RBC's to stack at the bottom of the tube.

Using a plastic pipette the supernatant was gently removed and the cells resuspended in another 7 volumes of PBS. Washing was repeated two times until the supernatant was clear. After the last wash the supernatant was removed.

A 10 mg/ml solution of IV was diluted to the desired concentration with PBS, e.g. for 5 mg/mL solution, 5 μl, +5 μL PBS.

For insertion of IV, RBCs were resuspended in the diluted (where necessary) solution at a ratio of 1 part solution to 3 part stacked cells. For each sample or control to be tested, 5 μL of sample or control solution was added to 15 μl resuspended cells in a 1.5 mL eppendorf.

The mixes were incubated:
3 hours at 21° C., mixing every hour, then for 18 hours at 4° C.; 2 hours at 37° C.;
4 hours at 37° C.;
Overnight (0/N) at 4° C.; or
Overnight (0/N) at 37° C.

Transformed RBCs were washed 3 times, by adding 1 mL PBS and centrifuging for 1 min at a low speed. Washing of the RBCs was then performed as described above. A 3% cell suspension was prepared by adding 0.3 μL of washed transformed RBCs to 97 μL PBS in a Kimble glass test tube.

In Kimble glass test tubes 30 μL of the 3% cell suspension+ 30 μl, 1% BSA/PBS diluted anti-HA antibody (Biogenesis, cat. no. 5029-9990) were mixed for test samples, or 30 μL 3% cell suspension+30 μL 1% BSA/PBS alone for controls. The mixtures were incubated at 37° C. for 30 min. The incubated mixtures were then centrifuged at high speed for 10 s and assessed for agglutination.

The samples were washed three times with PBS by repeated centrifugation at high speed and resuspension. 30 μL 1% BSA/PBS diluted donkey anti-sheep antibody (Invitrogen, cat. no. A-11015) was then added. The samples were then assessed for agglutination.

Figure 2:
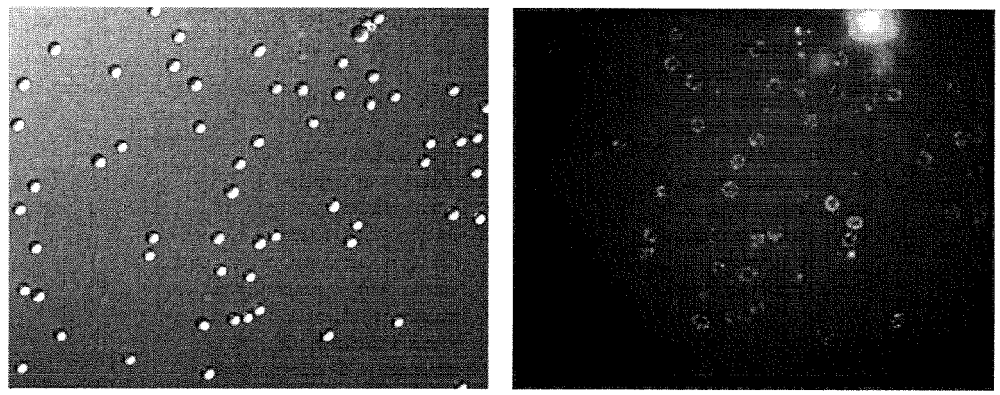
FIG. 2—Fluoresence microscopy of red blood cell membranes following insertion of HA-gar-Ad-DOPE (IV).

The results are presented in Table 1 and FIG. 2.

Reaction with Primary Antibody

Embryos from experiments were washed 4× in KH media taking care to rinse the micro handling pipette between each washing step. Embryos were then placed in microdrops with α-HA antibody and incubated in a 37° C. incubator (no $CO_2$) for 45 to 50 minutes.

Embryos were recovered and washed 4× in MV Wash.

Preparation of Alexa Fluor (AF) α-Sheep Microdrops

25 μL AF α-sheep (1:100dil) solution was pipetted into the middle of well of 4-well plate. The drop was covered with 0.8 mL mineral oil. A further 25 μL of AF α-sheep (1:100dil)

TABLE 1

Insertion of HA-gar-Ad-DOPE (IV) into red blood cell membranes

| Sample | Antibodies (α) | Insertion conditions | | | | | | |
|---|---|---|---|---|---|---|---|---|
| | | 3 hr 21° C., 18 hr 4° C. | | | | 2 hr 37° C. | | |
| | | 5 mg/mL | | | 1 mg/mL | 1 mg/mL | | |
| KODE15-20 | α-HA | 1:10 +++ | 1:50 + | 1:100 − | 1:10 +++ | 1:10 | 1:50 | 1:100 |
| | α-sheep | 1:20 ++ | 1:20 ++ | 1:20 − | 1:20 ++++ | 1:200 ++ | 1:200 (+) | 1:200 +(−) |
| KODE10-14 | α-HA | 1:10 +++ | 1:50 +/− | 1:100 − | 1:10 ++ | 1:10 +++ | 1:50 − | 1:100 − |
| | α-sheep | 1:20 ++++ | 1:20 − | 1:20 − | 1:20 +++ | 1:200 + | 1:200 − | 1:200 − |
| | Code | KBL6407E34 | KBL6407E35 | KBL6407E35 | KBL6407E34 | KBL6407E71 | KBL6407E71 | KBL6407E71 |

| Sample | Antibodies (α) | Insertion conditions | | | | |
|---|---|---|---|---|---|---|
| | | O/N 4° C. | O/N RT | 4 hr 37° C. | 2 hr 37° C. | O/N RT |
| | | 1 mg/mL | | | | 5 mg/mL |
| KODE15-20 | α-HA | 1:10 +++ | 1:10 +++ | 1:10 ++ | 1:10 + | 1:10 |
| | α-sheep | 1:200 +++ | 1:200 ++ | 1:200 ++ | 1:200 + | 1:20 + Fluorescence |
| KODE10-14 | α-HA | 1:10 ++ | 1:10 +++ | 1:10 ++ | 1:10 ++ | |
| | α-sheep | 1:200 ++ | 1:200 ++ | 1:200 + | 1:200 + | |
| | Code | KBL6407E86 | KBL6407E86 | KBL6407E86 | KBL6407E86 | KBL6407E111 |

Insertion of Ha-Gar-Ad-Dope (Iv) into Embryos
Preparation of α-HA Microdrops

25'μL α-HA (1:20dil) solution was pipetted into the middle of well of a 4-well plate. The drop was covered with 0.8 mL mineral oil. A further 25 μl of α-HA (1:20dil) solution was pipetted through the mineral oil onto the microdrop. Microdrops were incubated at 37° C.

Embryo Glue™ Treatment

Embryos were transferred to microdrops containing Embryo Glue™ and incubated at 37° C. (+5% CM for 20 min.

Preparation of Pronase Microdrops

25 μL 0.5% Pronase solution was pipetted into the middle of a well of a 4-well plate. The drop was covered with 0.8 mL mineral oil. A further 25 μl, of 0.5% pronase solution was pipetted through the mineral oil onto the microdrop. Microdrops were incubated at 37° C. (no $CO_2$).

Removal Of Zona Pellucida

Washed embryos were transferred from KH media to the pronase microdrops and incubated on a 37° C. (no $CO_2$) thermal plate until all the zona pellucidas were removed (c. 5 min.). The embryos were then washed 4× in KH media.

solution was pipetted through the mineral oil onto the microdrop. Microdrops are incubated at RT in the dark.

Washed embryos were placed in microdrops with AF α-sheep antibody. The four-well plates were then placed in the dark and incubated at room temperature (RT) for 30 minutes.

Embryos were recovered and washed 4× in MV Wash.

Imaging

Embryos were placed on a glass slide and covered with mineral oil. The slide was then stored in dark before imaging on a Olympus BX51 Fluorescent microscope.

Experiment 1

Embryos were placed in pre-warmed, de-gassed microdrops containing:
    $HA_{15\text{-}20\ mer}$-gar-Ad-DOPE (IV)
    $HA_{15\text{-}20\ mer}$-gar-Ad-DOPE (IV)+$HA_{15\text{-}20\ mer}$
    $HA_{15\text{-}20\ mer}$
    Control (media alone)

KC media alone

Embryos in microdrops were then incubated at 37° C. (+5% $CO_2$) for 24 hours.

Figure 3:
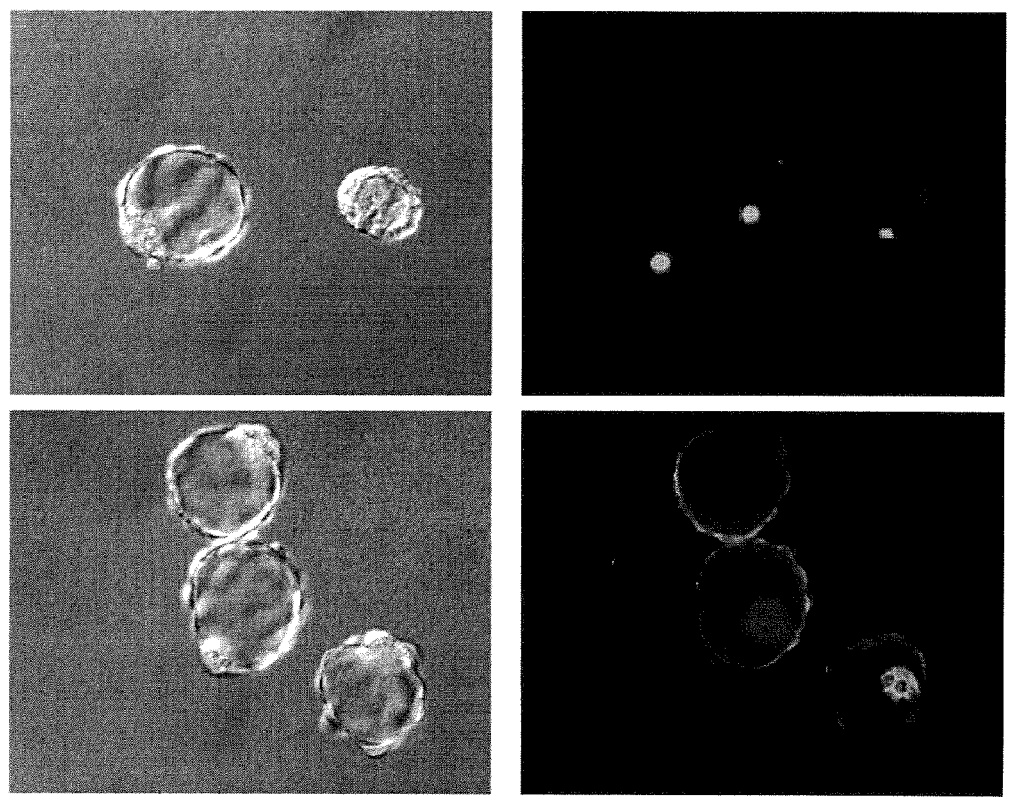
FIG. 3—Fluoresence microscopy of embryos following insertion of HA-gar-Ad-DOPE (IV): control (top); embryos following insertion (bottom).

The results are presented in FIG. 3.

Experiment 2

Embryos were placed in pre-warmed, de-gassed microdrops containing:
$HA_{15-20\ mer}$-gar-Ad-DOPE (IV) (zona pellucida removed);
High molecular weight (HMW) HA;
$HA_{15-20\ mer}$-gar-Ad-DOPE (Iv);
KC Media with Embryo Glue™;
KC media alone (control).

Embryos in microdrops were then incubated at 37° C. (+5% $CO_2$) overnight.

Figure 4:
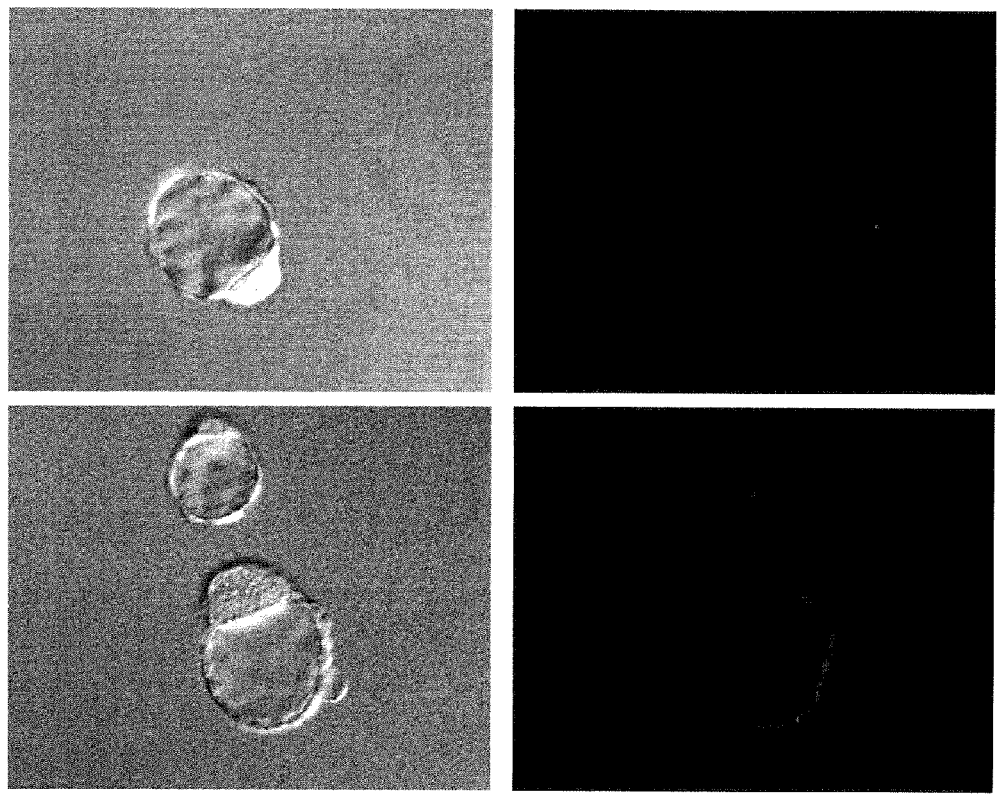
FIG. 4—Fluoresence microscopy of embryos following incubation with: Vitrolife Embryo Glue, 20 minutes (top); high molecular weight HA, 24 hours at 37° C. (bottom).
Figure 5:
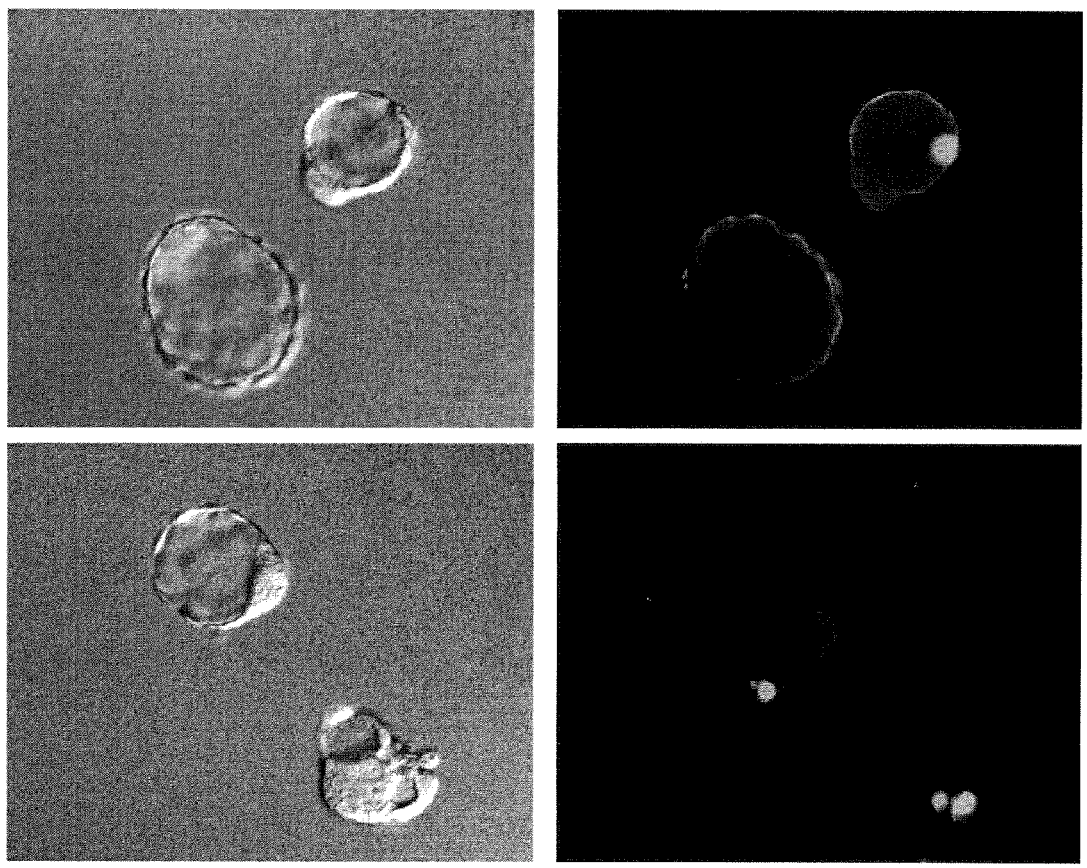
FIG. 5—Fluoresence microscopy of embryos following incubation with: HA-gar-Ad-DOPE (IV), 24 hours at 37° C. (top); media only, 24 hours at 37° C. (bottom).

The results are presented in Table 2 and FIGS. 4 and 5.

TABLE 2

Insertion of HA-gar-Ad-DOPE (IV) into embryos

| Treatment | α-HA | AF α-sheep | Number of embryos | Fluorescence |
|---|---|---|---|---|
| IV (zona pellucida removed) | 1:20 | 1:100 | 14 | 2+ |
| HMW HA | 1:20 | 1:100 | 10 | — |
| IV | 1:20 | 1:100 | 12 | 2+ |
| Embryo Glue ™ | 1:20 | 1:100 | 8 | — |
| Control | 1:20 | 1:100 | 12 | — |

Experiment 3

Embryos were placed in pre-warmed, de-gassed microdrops containing:
$HA_{15-20\ mer}$-gar-Ad-DOPE (IV) (zona pellucida removed)
KC media alone (zona pellucida removed) (control)

Embryos in microdrops were then incubated at 37° C. (+5% $CO_2$) for 2 hours. Retention of $HA_{15-2\ mer}$-gar-Ad-DOPE (IV) was observed after 2, 5 and 24 hours.

Figure 6:
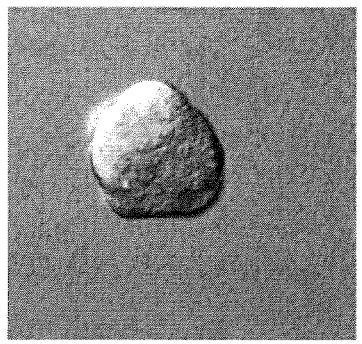
FIG. 6—Fluoresence microscopy of embryos following removal of the zona pellucida and incubation with: HA-gar-Ad-DOPE (IV), 2 hours at 37° C. (top and middle); media only, 2 hours at 37° C. (bottom).
Figure 6:
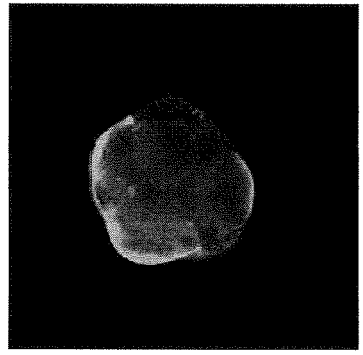
Figure 6:
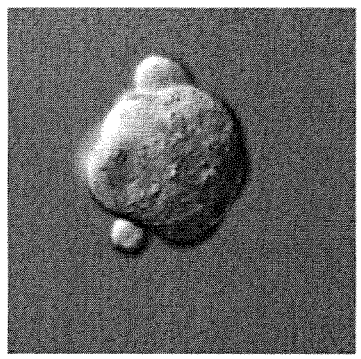
Figure 6:
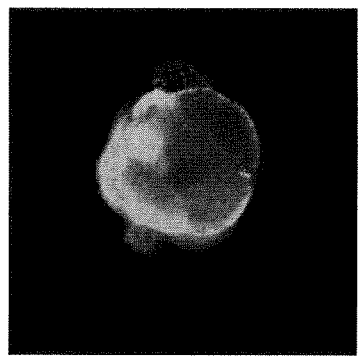
Figure 6:
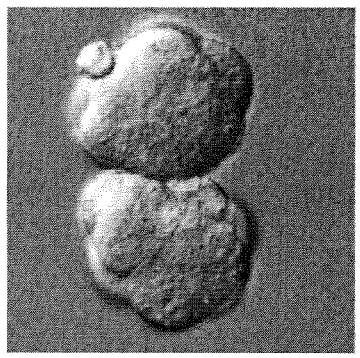
Figure 6:
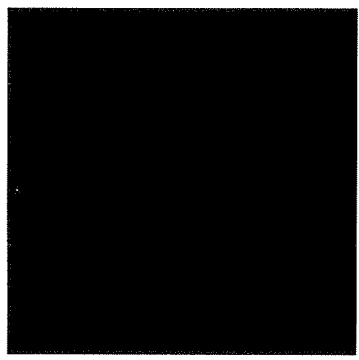
Figure 7:
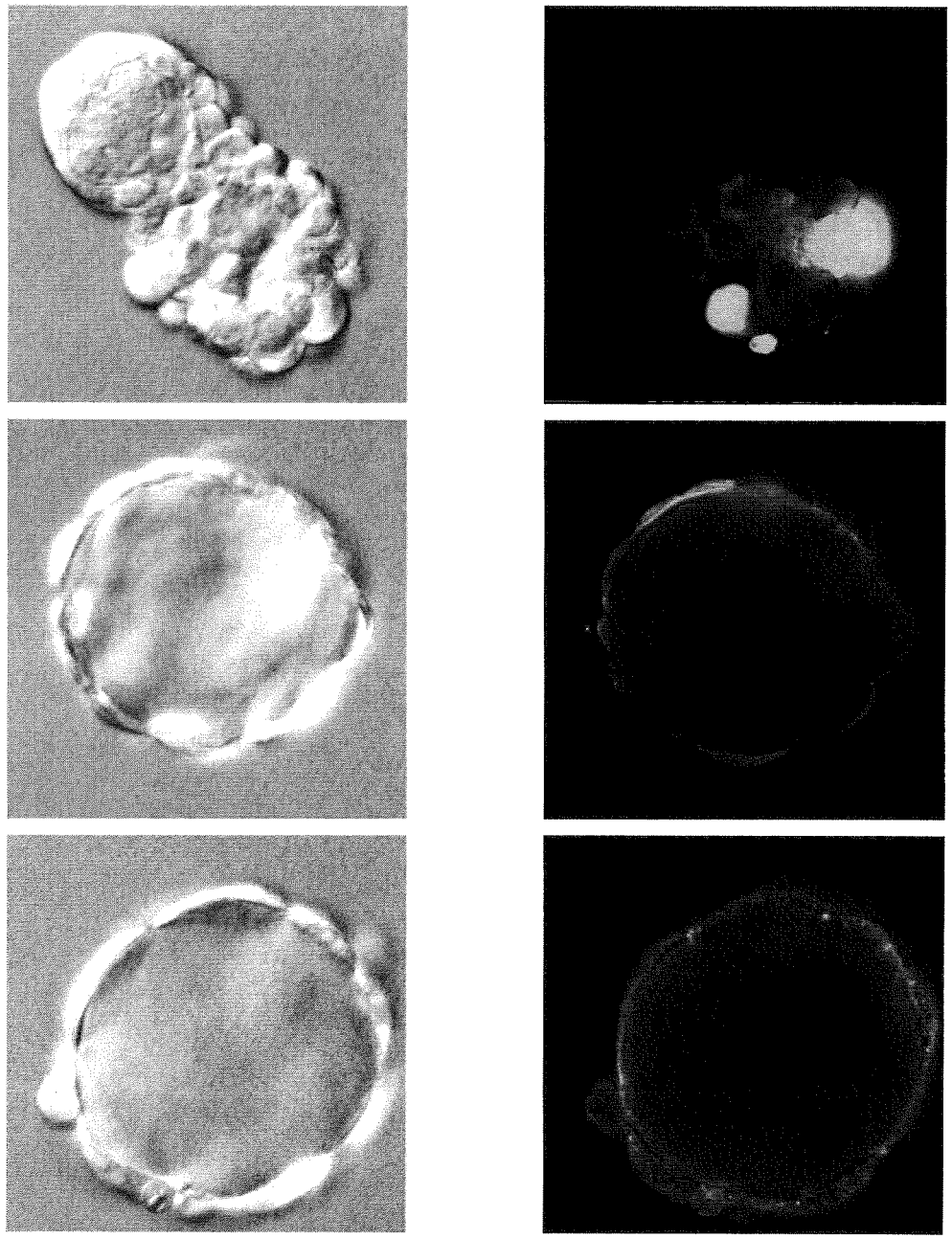
FIG. 7—Fluoresence microscopy of embryos incubated with HA-gar-Ad-DOPE (IV) (2 hours at 37° C.) after: 24 hours post incubation (top); 5 hours post incubation (middle); and 2 hours post incubation (bottom).
Figure 8:
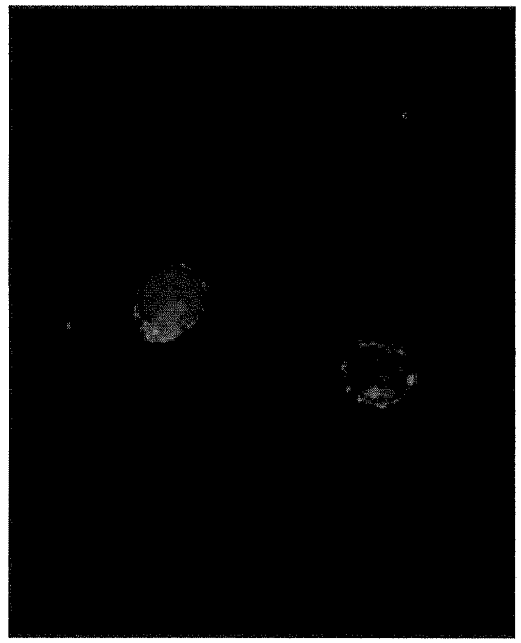
FIG. 8—DIC image of unmodified embryos. Right plate: Same image but viewed as merged NIB/WIG fluorescent images. Result shows zero attachment of epithelial cells to the embryo (red).
Figure 8:
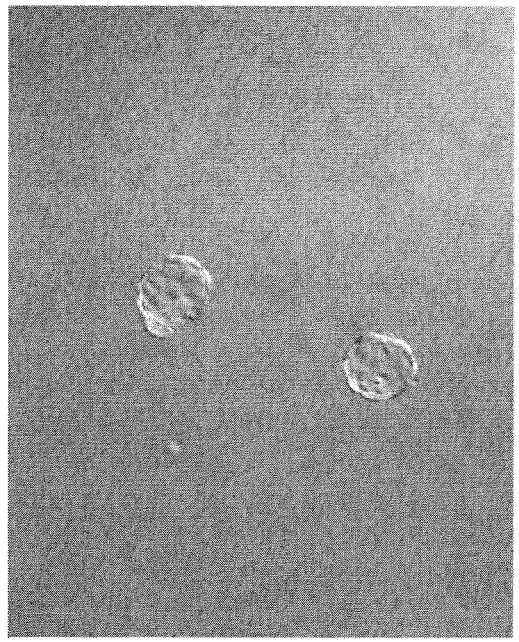
Figure 9:
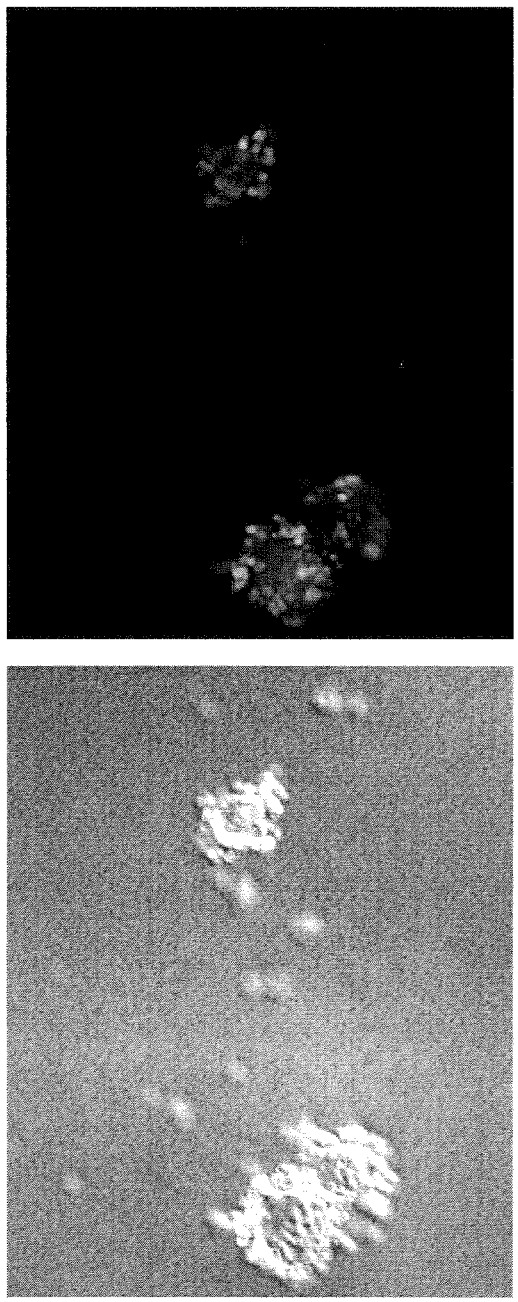
FIG. 9—DIC image of VVA modified embryos. Right plate: Same image but viewed as merged WIB/WIG fluorescent images. Result shows positive binding of endometrial cells (green) to embryos (red). Attachment numbers from left to right are 35, 20 and 27.
Figure 10:
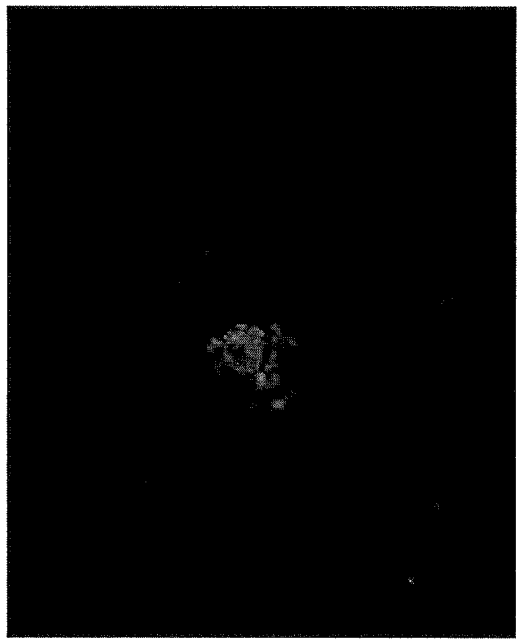
FIG. 10—FIG. 10. DIC image of HA$_{15-20\ mer}$-gar-Ad-DOPE (IV) modified embryo. Right plate: Same image but viewed as merged WIB/WIG fluorescent images. Result shows positive binding of 10 endometrial cells (green) to the embryo (red).
Figure 10:
Figure 11:
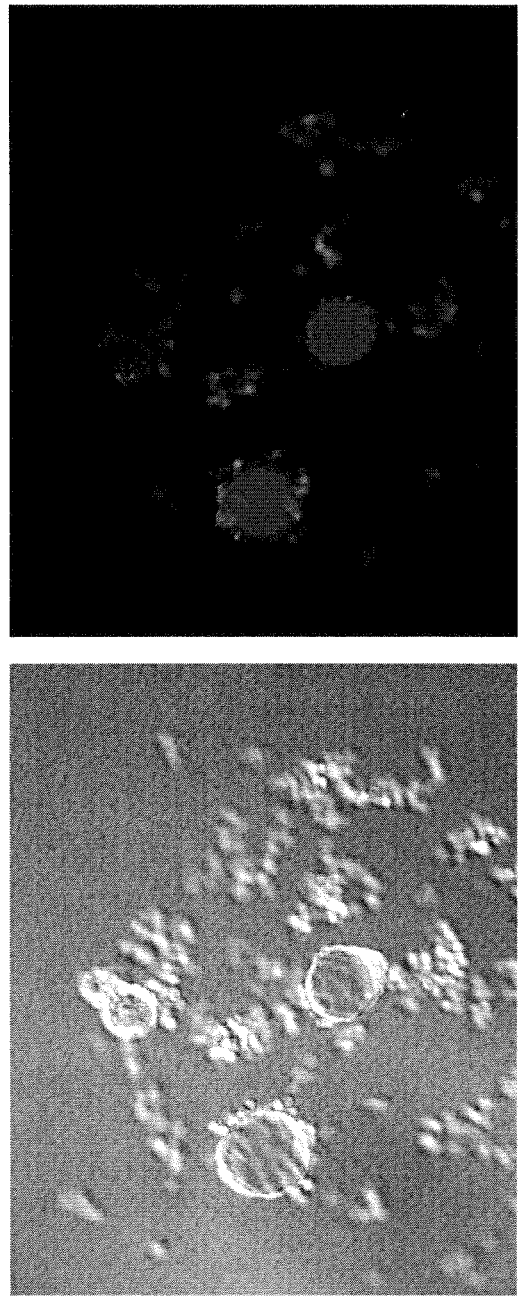
FIG. 11—FIG. 11. DIC image of HA$_{15-20\ mer}$-gar-Ad-DOPE (IV) modified embryos. Right plate: Same image but viewed as merged WIB/WIG fluorescent images. Result shows positive binding of endometrial cells (green) to embryos (red). Attachment numbers from left to right are 15, 8 and 9.
Figure 12:
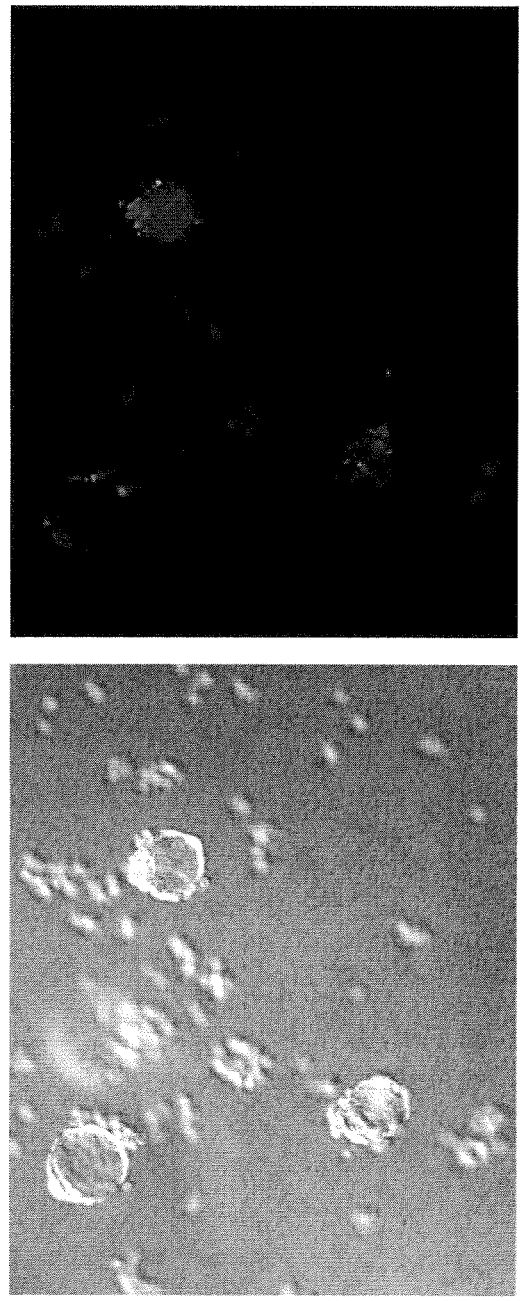
FIG. 12-DIC image of HA$_{15-20\ mer}$-gar-Ad-DOPE (IV) modified embryos. Right plate: Same image but viewed as merged WIB/WIG fluorescent images. Result shows positive binding of endometrial cells (green) to embryos (red). Attachment numbers from left to right are 8, 8 and 5.

The results are presented in FIGS. 6 and 7.

$HA_{15-20\ mer}$-gar-Ad-DOPE (IV) In Vitro Murine Embryo Toxicity Studies

Studies were performed to assess the effects of overnight insertion of $HA_{15-20\ mer}$-gar-Ad-DOPE (IV) on murine embryo morphology and development.

Preparation of Mouse Embryos

Pre-pubescent C57/CBA F1 generation mice (21-30 days old) were superovulated by intrapertoneal injection of 5IU of FSH (Folligon, Intravet, NZ) between 15:30 and 17:30, and 48 hours later with 5IU of human chorionic gonadotrophin (Chorulon, Intravet, NZ).

Each donor mouse was placed with a CBA male stud of proven fertility and checked for a seminal plug the following morning (day 0.5 post-coitus).

On day 1.5 post-coitus donor mice were sacrificed by cervical dislocation. Uterine horns including the oviduct were excised from the abdomen and placed on a sterile Petri dish.

Two-cell embryos were flushed from the oviduct using in-house handling media (HM), collected and cultured in human embryo culture media (HECM) in 5% $CO_2$ at 37° C. until time of the experiment.

Preparing Experimental and Control Microdrops

Both sets of microdrops were prepared and equilibrated in 5% $CO_2$ at 37° C. for at least 2 hours before use.

Experimental microdrops were 2 mg/mL $HA_{15-20\ mer}$-gar-Ad-DOPE (IV). 30 μL of HECM was placed centrally in a well of a 4-well culture dish. The drop was then overlayed with 0.9 mL sterile mineral oil and 20 μL of stock $HA_{15-20\ mer}$-gar-Ad-DOPE (IV) at 5 mg/mL in HECM was added (mixed gently by pipetting).

Control drops were made in a similar fashion, but 20111, of HECM was added after the sterile mineral oil was overlaid (whole drop contained HECM).

Preparation of Embryos

On day 2.5 post coitus, 20 healthy randomly selected embryos were placed into each group and incubated in 5% $CO_2$ at 37° C. overnight in either $HA_{15-20\ mer}$-gar-Ad-DOPE (IV)-containing or control media.

All embryos (now day 3.5) were washed in 37° C. HM and placed into 1 mL of HM kept on a 37° C. heat plate under aluminium foil (keeping groups separate).

Embryos were transferred in HECM microdrops and incubated in 5% $CO_2$ at 37° C. and assessed for embryo morphology or development following further culture Grading of Murine Blastocysts Blastocysts were graded on Day 3.5, Day 4.5 and Day 5.5 post coitus. Blastocysts were graded on two separate scales:
i) the rate of embryo development, predicted by the size of the fluid filled blastocoel; and
ii) the health of the embryos, related to the amount of degradation/fragmentation visualised.

The grading system used to describe the rate of embryo development was as follows:

| Blastocyst score | Visual factors |
|---|---|
| 5 | No blastocoel |
| 4 | Blastocoel less than half the volume of the embryo |
| 3 | Blastocoel greater than half the volume of the embryo |
| 2 | Blastocoel completely fills the embryo |
| 1 | Blastocoel volume is larger than that of an early blastocyst |
| Hatching | Hatching blastocyst |
| Hatched | Fully hatched from zona pellucida |

The alphabetical grading used to predict the health of the embryo was as follows:

| Blastocyst degradation | Visual factors |
|---|---|
| C | Dark degenerative material, irregular sizing of blastomere cells, highly distorted shape |
| B | Minimal degenerative material Minor cytoplasmic fragmentation, minimal distortion of blastomere size and blastocyst shape |
| A | No degenerative material, uniform blastomere sizes, uniform blastocyst shape |

Combining these two scales together gave 15 blastocyst grades from the poorest 5C to the healthiest 1A.

In practice the 1A and 2A were often grouped together as the marginal visual difference between these two and discrepancy noted between observers meant that statistically it was more credible to group these together.

Results

TABLE 3

Summarising embryo grade on days 3.5, 4.5 and 5.5 post coitus after an overnight incubation in 2 mg/mL $HA_{15\text{-}20\,mer}$-gar-Ad-DOPE (IV)

| Embryo Grade | Control D3.5 | D4.5 | D5.5 | $HA_{15\text{-}20\,mer}$-gar-Ad-DOPE (IV) D3.5 | D4.5 | D5.5 |
|---|---|---|---|---|---|---|
| 5A | 149 | 0 | 0 | 155 | 2 | 1 |
| 4A | 29 | 0 | 0 | 24 | 0 | 0 |
| 3A | 5 | 0 | 0 | 9 | 0 | 0 |
| 2A | 5 | 6 | 1 | 3 | 3 | 0 |
| 1A | 3 | 11 | 0 | 3 | 6 | 2 |
| HgB | 8 | 115 | 116 | 5 | 111 | 100 |
| HdB | 0 | 6 | 16 | 0 | 5 | 19 |
| All B Grade | 7 | 11 | 6 | 6 | 12 | 2 |
| All C Grade | 0 | 2 | 1 | 0 | 5 | 3 |
| Total | 206 | 151 | 140 | 205 | 144 | 127 |

Summary

The results showed that $HA_{15\text{-}20\,mer}$-gar-Ad-DOPE (IV) modified murine embryos which were in vitro cultured to day 5.5 post coitus showed no untoward consequences in morphology or development.

$HA_{15\text{-}20\,mer}$-gar-Ad-Dope (Iv) In Vivo Toxicity Studies Using Murine Embryo Transfers Studies were performed to assess the effects of modifying murine embryos with $HA_{15\text{-}20\,mer}$-gar-Ad-DOPE (IV) on implantation and viability when transferred into pseudo-pregnant mice.

Methodology

Mouse embryos experimental and control microdrops, and modified embryos were prepared as per the methods described above ($HA_{15\text{-}20\,mer}$-gar-Ad-DOPE (IV) in vitro murine embryo toxicity studies).

On day 3.5 post coitus 5 embryos were selected from the $HA_{15\text{-}20\,mer}$-gar-Ad-DOPE (IV) modified embryo and 5 from the unmodified embryo groups.

The selection process used a computer generated randomised list (specifying the embryos, order in which groups were transferred and the side groups were transferred into).

Embryos were placed into 1 mL of HM kept on a 37° C. heat plate under aluminium foil until transfer. Groups were kept in separate wells.

Preparation of Pseudo-Pregnant Recipient Mice

In order to obtain a receptive endometrium within a recipient mouse, the recipient must be mated with a vasectomised male mouse of proven sterility. The act of coitus maintains the corpus luteum of ovulated follicles and appropriate levels of progesterone for implantation.

On day 0.5 post coitus of the donor mice, approximately 8 CBA/C57 F1 generation females between 60 and 100 days old and in estrus were selected from a large pool and mated with vasectomised CBA male mice.

Recipient mice were checked for seminal plugs the following morning, denoting pseudo-pregnancy (day 0.5 post coitus). The specified programming meant recipient mice were asynchronous by minus 1 day compared to the embryos. The rationale was that the embryos would "wait" for a receptive endometrium, but a receptive endometrium would not "wait" for embryo.

Mice were kept in separate cages until the day of transfer.

Embryo Transfer in a Dual Horn Fertile Model

Day 3.5 post coitus embryos were transferred into day 2.5 post coitus recipients. As described above the order and side of transfer for each group was determined by computer generated randomised lists.

Recipient mice were anaesthetised with 0.8 mL of Avertin (made in-house) and an incision was made on the side of the abdomen, just above the hip. The ovary was secured by grasping the fat pad above it with a serrafin clamp and withdrawing outside of the body.

All surgery was preformed on a 37° C. heat plate.

A 29 g needle was used to create a hole through the uterine horn. Five embryos were loaded into a fire-pulled and polished capillary pipette (approx. 150-170 μm in diameter) with mineral oil and air gaps for stabilization.

The pipette was inserted into the uterine horn through the pre-prepared hole and expelled until an air-gap was visible. The uterine horn and ovary were replaced into the abdominal cavity and the body wall and skin were sutured closed.

Mice were identified through ear marks and observed until conscious.

Assessment of Fetal Outcomes

Recipients were euthanized on day 15 post-embryo transfer. An incision was made in the abdomen exposing the entire uterus. Viability of each fetus was checked by gently pinching with forceps, followed by excision of the uterus.

Each fetus was excised out of the uterine horns and separated from placenta. Each fetus and its corresponding placenta were weighed.

Results

A summary of the results is provided in Table 4.

TABLE 4

Summary of 14 experiments transferring 2 mg/ml overnight HA15-20mer modified embryos (exp) and unmodified embryos (ctrl) into the left or right horns of a recipient mouse.

| Variable | Fetus $HA_{15\text{-}20\,mer}$-gar-Ad-DOPE (IV) | Ctrl |
|---|---|---|
| embryos introduced | 70 | 70 |
| Mean weight (g) | 0.96 | 0.98 |
| Resorptions | 8.00 | 10.00 |
| Losses | 8.00 | 7.00 |
| Implant sites | 62 | 63 |
| Viable fetuses | 54 | 53 |
| Fetus resorption | 8 | 10 |
| embryo loss | 8 | 7 |
| Mean fetus weight (g) | 0.96 | 0.98 |
| SD (fetus weight) | 0.099 | 0.095 |
| Mean placenta weight (g) | 0.11 | 0.11 |

Summary

When comparing the implantation rates of experimental and control groups through binary logistic regression, a p-value of 0.530 resulted. Thus there was no significant difference between the two groups.

When comparing the fetal weights of experimental and control groups through general linear modelling, a p-value of 0.140 resulted. Thus, there was no significant difference between the two groups.

These results show that in a fertile animal there are no untoward consequences of $HA_{15\text{-}10\ mer}$-gar-Ad-DOPE (IV) modification on pregnancy or in utero development.

Resetting of $HA_{15\text{-}20\ mer}$-Gar-Ad-Dope (IV) Inserted Murine Embryos With Single Cell HEC-1A Human Epithelial Cells Studies were performed to determine the level of adherence of single cell human epithelial cells from endometrial cell line HEC-1A (Human Endometrial Carcinoma sub-adherent cell line, ATCC HTB-112) to murine embryos inserted with $HA_{15\text{-}20\ mer}$-gar-Ad-DOPE (IV) in vitro.

Embryos at the hatching to hatched stage had their zona pellucidae removed and were incubated with:
A) $HA_{15\text{-}20\ mer}$-gar-Ad-DOPE (IV) (experimental);
B) media alone (blank—HECM, human embryo culture media); or
C) lectin VVA (*Vicia villosa*, Milton Adams BA 4601-2).

Embryos were then incubated with epithelial cells and visualized for attachment using fluorescence microscopy.

Treatment Group C served as a positive control of maximal rosetting.

Embryos were pre-stained with a fluorescent dye SNARF (red label, 5-(and -6)-chloromethyl SNARF®-1, acetate, Molecular Probes #06826) and endometrial epithelial cells were stained with fluorescent dye CMFDA (green label—CellTracker™ Green CMFDA, 5-chloromethylfluorescein diacetate, Molecular Probes #C7025) in order to easily visualize attachment of epithelial cells to embryos.

| Group | Treatment |
|---|---|
| A. Experimental | $HA_{15\text{-}20\ mer}$-gar-Ad-DOPE (IV) (2 mg/mL) in HECM |
| B. Blank (Negative control) | HECM |
| C. Rosette Positive control | Lectin VVA (0.2 mg/mL) in HECM |

Preparation of Murine Embryos and Microdrops

Murine embryos and microdrops were prepared as per the methods described above ($HA_{15\text{-}20\ mer}$-gar-Ad-DOPE (IV) in vitro murine embryo toxicity studies) but with HECM media (with or without VVA)

Removal of Zona Pellucida

Embryos were transferred to 0.5% pronase (Sigma #P8811) 50 µL microdrops and placed in a 37° C. incubator for 6 minutes or until the zona pellucidae (ZP) were removed (checked every 2 minutes).

Embryos were washed 3× in 50 µL in-house handling media (HM) drops and transferred to HM holding well (1 mL).

Staining Embryos with SNARF

The following steps were performed protected from light.

Embryos were transferred to 2 µM SNARF 50 µL microdrops and incubated for 40 minutes in a 37° C. incubator, in an aluminium foil covered container.

The embryos were then washed 2× in HM media.

Embryos were transferred to HM media microdrops and incubated a further 40 minutes in the 37° C. incubator.

Modification of Embryos

The following steps were performed protected from light.

Embryos transferred to Group A microdrops were incubated at 37° C.+5% $CO_2$ for 2 hr.

Embryos transferred to Group B microdrops were incubated at 37° C.+5% $CO_2$ for 2 hr.

Embryos transferred to Group C microdrops were incubated at 37° C. 5% $CO_2$ for 40 min.

Treated embryos were washed 1× HM media (1 mL), transferred to HECM Microdrop, and incubated at 37° C. 5% $CO_2$ for a further hour and 10 min.

Staining HEC-1A Epithelial Cells

The following steps were performed protected from light. Cells were centrifuged 200 g for 10 min and the supernatant removed.

500 µL 3 µM CMFDA in 3% PVP (polyvinyl pyrrolidone, Medicult AB, #10890001)/1×PBS was added to cells and the cell gently resuspended.

Cells were incubated in a 37° C. shaking water bath for 45 min (resuspended occasionally).

Cells were centrifuged 200 g for 10 min and the supernatant removed.

Cells were gently resuspended in 500 µL Calcium and Magnesium Free Hanks Balanced Salt Solution (CMF-HBSS, Gibco-Invitrogen, #14170112) plus 2% Fetal Bovine Serum (FBS, Gibco-Invitrogen, #10091-130).

Cells were incubated in a 37° C. shaking water bath for a further 30 min.

The epithelial cells were then washed 2× by resuspending cells in CMF-HBSS-2% FBS, centrifuging 200 g for 10 min, and removing supernatant. Washing was repeated.

Preparation of Terasaki Plates

A row number and column letter was allocate to each experimental and control group, marking clearly.

8 µl, of HM Media was aliquotted into each well identified for use.

Incubation of Embryos and HEC-1a Epithelial Cells

The following steps were performed in the dark as much as possible.

The epithelial cells were used at $20\text{-}25\times10^6$ cells per mL.

Embryos from each group were placed in their respective wells on the Terasaki tray, ensuring that there were no more than 3 embryos per well and the embryos were separated.

Using a wide-bore handling pipette, the re-suspended epithelial cells were gently aspirated (gently mixing prior to use to remove clumps) over the embryos ensuring that epithelial cells surrounded the embryos and covered the base of the well.

The lid was placed firmly on Terasaki tray and the cells were incubated at room temperature for 30 minutes covered in aluminium foil.

Wells were checked after 10 min and every 5 minutes thereafter to ensure cells did not dry out.

Visualisation of "Rosetted" Embryos

The following steps were performed in the dark as much as possible.

Using a wide-bore handling pipette embryo and epithelial cells were gently transferred to 1 mL HM media (pre-warmed).

A 5 µl, drop of HM media was placed onto a microscope slide.

Embryos were transferred into the HM media drop on the microscope slide (being careful not to transfer free epithelial cells) and covered with mineral oil (<10 µL) by placing around the circumference of the media and then gently covering the top of the media.

Each microscope slide was viewed under an Olympus BX51 fluorescent microscope under 100× magnification, taking three pictures of each embryo; one DIC (Differential Interference Contrast microscopy), and two fluorescent (WIB and WIG filters, 550 nm and 620 nm respectively).

The two fluorescent images were merged using Olysia BioReport. (FIGS. 8 to 12)

Scoring Adherence

The number of endometrial cells attached to each embryo at the centre plane of focus was recorded for every embryo. Results are presented in Tables 5 to 7.

TABLE 5

| Epithelial cells attached | Rosette Assay (n) | | Rosette Control (VVA) |
|---|---|---|---|
| | Unmodified | HA15-20mer | |
| 0 | 11 | 4 | 0 |
| 1 | 2 | 3 | 0 |
| 2-3 | 3 | 4 | 0 |
| 4-5 | 2 | 4 | 0 |
| 6-10 | 0 | 8 | 1 |
| 11-20 | 0 | 1 | 5 |
| 20-40 | 0 | 0 | 10 |
| Mean* | 1.06 | 4.73 | 23.5 |

TABLE 6

| Epithelial cells attached | Rosette Assay (%) | | Rosette Control (VVA) |
|---|---|---|---|
| | Unmodified | HA15-20mer | |
| 0 | 61% | 17% | 0% |
| 1 | 11% | 13% | 0% |
| 2-3 | 17% | 17% | 0% |
| 4-5 | 11% | 17% | 0% |
| 6-10 | 0% | 33% | 6% |
| 11-20 | 0% | 4% | 31% |
| 20-40 | 0% | 0% | 63% |

TABLE 7

| Epithelial cells attached | Rosette Assay (mean) | | Rosette Control (VVA) |
|---|---|---|---|
| | Unmodified | HA15-20mer | |
| Mean | 1.06 | 4.73 | 23.5 |
| % of Max | 4.5% | 20.1% | 100% |

The rosette assay demonstrated at least a four-fold increase in attachment of epithelial cells to $HA_{15\text{-}20\ mer}$-gar-Ad-DOPE (IV) modified embryos.

$H_{15\text{-}20\ mer}$-gar-Ad-DOPE (IV) Transformed Red Blood Cells Incubated with HMW HA, Bovine Serum Albumin Solutions or Human Serum Studies were performed to test whether $HA_{15\text{-}20\ mer}$-gar-Ad-DOPE (IV) transformed red blood cells (RBCs) associated with high molecular weight HA (HMW HA), albumin or compatible serum which would cause them to agglutinate/aggregate.

Insertion of $HA_{15\text{-}20\ mer}$-Gar-Ad-Dope (IV) into RBCs $HA_{15\text{-}20\ mer}$-gar-Ad-DOPE (IV) @ 10 mg/ml, to 5 mg/ml, was diluted in Celpresol (CSL #063321301).

15 µL of washed group 0 RBC, then 5 µL of $HA_{15\text{-}20\ mer}$-gar-Ad-DOPE (IV) or Celpresol (untreated) was added to an eppendorf tube and mixed.

Tubes were incubated at room temperature for 3 hr, then 4° C. overnight with occasional mixing.

Transformed RBCs were washed two times with PBS and then suspended as 5% in Celpresol.

High Molecular Weight HA (HMW RA), Bovine Serum Albumin (BSA) and Serum Solutions.

HMW HA was hyaluronic acid sodium salt from *Streptococcus equi* from Fluke BioChemika Cat#53747 (MW 1.5-1.8×10⁶ Da). Solutions of 0.5 and 2.5 mg/ml were prepared in Celpresol.

BSA was bovine serum albumin Gibco Cat #30063-572. Solutions of 2%, 4%, 6%, 8% and 10% (w/v) were prepared in PBS.

Serum was human serum not containing antibodies directed against the group 0 cells.

Incubating Transformed RBCs with HMW Ha Solutions

5% suspensions were made from washed transformed group 0 RBCs.

30 µL $HA_{15\text{-}20\ mer}$-gar-Ad-DOPE (IV) RBC or untreated RBC was added to 60 µL HMW HA, bovine serum albumin solution or human serum, in duplicate.

Samples were either:

centrifuged for 10 s in an immufuge then assessed for agglutination; or incubated 30 mins at 37° C., centrifuged and then assessed for agglutination.

The results showed that in the presence of high molecular weight protein (albumin) or high molecular weight HA cells coated with HA as $HA_{15\text{-}20\ mer}$-gar-Ad-DOPE (IV) are able to interact as visualised by agglutination via non antibody mediated interactions.

Although the invention has been described by way of exemplary embodiments it should be appreciated that variations and modifications may be made without departing from the scope of the invention. Furthermore where known equivalents exist to specific features, such equivalents are incorporated as if specifically referred to in this specification.

INDUSTRIAL APPLICABILITY

The invention has application in the preparation of media and medicinal formulations.

TABLE 8

Agglutination scores - $HA_{15\text{-}20\ mer}$-gar-Ad-DOPE (IV) RBC Immediate Centrifugation

| HMW HA mg/mL | $HA_{15\text{-}20\ mer}$-gar-Ad-DOPE (IV) RBC RT | | Untreated RBC RT | |
|---|---|---|---|---|
| | 1 | 2 | 3 | 4 |
| 0 | — | — | — | — |
| 0.5 | — | — | — | — |
| 2.5 | 2+ | 2+ | — | — |

TABLE 9

Agglutination scores - $HA_{15-20\ mer}$-gar-Ad-DOPE
(IV) RBC 37° C. incubation then centrifugation

| HMW HA mg/mL | $HA_{15-20\ mer}$-gar-Ad-DOPE (IV) RBC 37° C. | | Untreated RBC 37° C. | |
|---|---|---|---|---|
| | 1 | 2 | 3 | 4 |
| 0 | — | — | — | — |
| 0.5 | — | — | — | — |
| 2.5 | 1+ | 3+ | — | — |

TABLE 10

Agglutination scores - BSA Immediate Centrifugation

| HMW HA mg/mL | $HA_{15-20\ mer}$-gar-Ad-DOPE (IV) RBC RT | | Untreated RBC RT | |
|---|---|---|---|---|
| | 1 | 2 | 3 | 4 |
| 2% | — | — | — | — |
| 4% | vw | vw | — | — |
| 6% | 2+ | 2+ | — | — |
| 8% | 2+ | 2+ | — | — |
| 10% | 3+ | 3+ | — | — |

TABLE 11

Agglutination scores - BSA 37° C. incubation then Centrifugation

| HMW HA mg/mL | $HA_{15-20\ mer}$-gar-Ad-DOPE (IV) RBC 37° C. | | Untreated RBC 37° C. | |
|---|---|---|---|---|
| | 1 | 2 | 3 | 4 |
| 2% | — | — | — | — |
| 4% | 1+ | 1+ | — | — |
| 6% | 2+ | 2+ | — | — |
| 8% | 3+ | 3+ | — | — |
| 10% | 3+ | 3+ | — | — |

TABLE 12

Agglutination scores - Serum Immediate Centrifugation

| Serum Sample | $HA_{15-20\ mer}$-gar-Ad-DOPE (IV) RBC RT | | Untreated RBC RT | |
|---|---|---|---|---|
| | 1 | 2 | 3 | 4 |
| 1 | 3+ | 2+ | — | — |
| 2 | 4+ | 3+ | — | — |
| 3 | 4+ | 4+ | — | — |
| 4 | 4+ | 4+ | — | — |
| 5 | 4+ | 4+ | — | — |
| 6 | 4+ | 4+ | — | — |
| 7 | 4+ | 4+ | — | — |
| 8 | 4+ | 4+ | — | — |

REFERENCES

Lee C N, Ax R L. Concentration and composition of glycosaminoglycans in the female bovine reproductive tract. J Dairy Sci 1984; 67: 2006-2009

Furnus C C, De Matos D G and Martinez A G. Effect of HA on development of in vitro produced bovine embryos. Theriogenology 49:1489-1499, 1998

Toole B P. Proteoglycans and hyaluronan in morphogenesis and differentiation. In: Hay ED (ed), Cell Biology of extracellular matrix. New York: Plenum Press, 1991; 305-339

Akira Tawada, Takahiro Masa, Yoji Oonuki, Atsushi Watanabe, Uuji Matsuzaki, and Akira Asari. Large-scale preparation, purification, and characterization of hyaluronan oligosaccharides from 4-mers to 52-mers. Glycobiology vol. 12 no. 7 pp. 421-426, 2002

Lesley, Jayne, Hascall, Vincent C, Tammi, Markku, Hyman, Robert. Hyaluronan Binding by Cell Surface CD44. The Journal of Biological Chemistry Vol. 275, NO. 35, Issue of September 1, pp. 26967-26975, 2000

Aruffo, Alejandro, Stamenkovic, Ivan, Melnick, Michael, Underhill, Charles B and Brian Seed. CD44 Is the Principal Cell Surface Receptor for Hyaluronate. Cell, Vol. 61, 1303-1313, Jun. 29, 1990

Gardner, David K, Rodriegez-Martinez, Heriberto and Lane, Michelle. Fetal development after transfer is increased by replacing protein with the glycosaminoglycan hyaluronan for mouse embryo culture and transfer. Human Reproduction vol. 14 no. 10 pp. 2575-2580, 1999.

The invention claimed is:

1. A water soluble construct of the structure F—$S_1$-$S_2$-L where: F—$S_1$ is an oligomer of β1-4 linked disaccharide units of glucuronic acid β1-3N-acetylglucosamine including a terminal glycamine residue; $S_2$ is —CO(CH$_2$)$_3$CO—, —CO(CH$_2$)$_4$CO— or —CO(CH$_2$)$_5$CO—; L is a phosphatidylethanolamine; and F—$S_1$, $S_2$ and L are covalently linked.

2. The construct of claim 1 where the oligomer is 15 to 20 mer.

3. The construct of claim 2 where L is derived from one or more cis-desaturated fatty acids.

4. The construct of claim 3 where L is 1,2-O-dioleoyl-sn-glycero-3-phosphatidylethanolamine.

5. The construct of claim 1 of the structure:

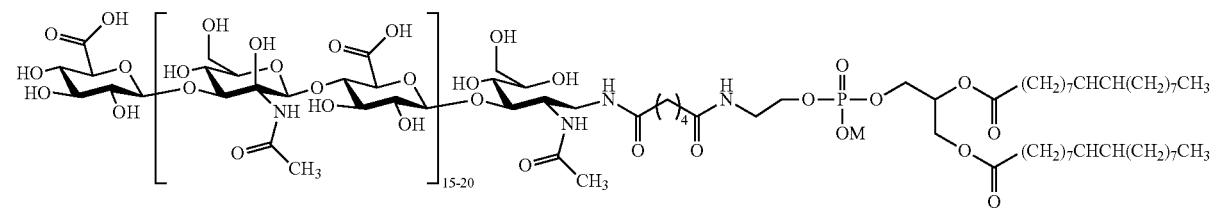

where M is a monovalent cation.

* * * * *